United States Patent
Robertus et al.

(10) Patent No.: US 6,562,969 B1
(45) Date of Patent: May 13, 2003

(54) RICIN INHIBITORS AND METHODS FOR USE THEREOF

(75) Inventors: Jon Robertus, Austin, TX (US); Sean Kerwin, Round Rock, TX (US); Xinjian Yan, College Station, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 09/535,460

(22) Filed: Mar. 24, 2000

Related U.S. Application Data

(63) Continuation-in-part of application No. 09/118,535, filed on Jul. 17, 1998, now Pat. No. 6,177,280, which is a continuation-in-part of application No. 08/773,398, filed on Dec. 24, 1996, now abandoned.

(51) Int. Cl.⁷ .................. C07D 487/02; C07D 473/00
(52) U.S. Cl. .................. 544/280; 544/262; 544/265
(58) Field of Search .................. 544/262, 280, 544/276, 320, 326, 265

(56) References Cited

U.S. PATENT DOCUMENTS 4,371,514 A * 2/1983 Nagatsu et al.
5,219,926 A * 6/1993 Lindman et al.
5,512,282 A * 4/1996 Krivan et al.

OTHER PUBLICATIONS

X. Yan et al, J. Mol. Biol. (1997) 266, 1043–1049.*
P. Stecher, The Merck Index of Chemicals and Drugs (1960), 501 and 871, Merck & Co., Inc.*
Y. Sung et al, Chem. Abstr. 1994: 208153.*
F. Seela et al, Chem. Abstr. 1977: 423203.*
Chem. Abstr. 105: 153031.*

* cited by examiner

*Primary Examiner*—Mary E. Ceperley
(74) *Attorney, Agent, or Firm*—Benjamin Aaron Adler

(57) ABSTRACT

Ricin A-chain is an N-glycosidase that attacks ribosomal RNA at a highly conserved adenine residue. Crystallographic studies show that not only adenine and formycin, but also pterin-based rings can bind in the ricin active site. For a better understanding of the recognition mode between ricin, and adenine-like rings, the interaction energies and geometries were calculated for a number of complexes. Shiga toxin, a compound essentially identical to the protein originally isolated from *Shigella dysenteniae*, has an active protein chain that is a homologue of the ricin active chain, and catalyzes the same depurination reaction. The present invention is drawn to identifying inhibitors of ricin and Shiga toxin, using methods molecular mechanics and ab initio methods and using the identified inhibitors as antidotes to ricin or Shiga toxin, or to facilitate immunotoxin treatment by controlling non-specific cytotoxicity.

1 Claim, 31 Drawing Sheets formycin adenine(1)

pterin(1)

guanine(1)

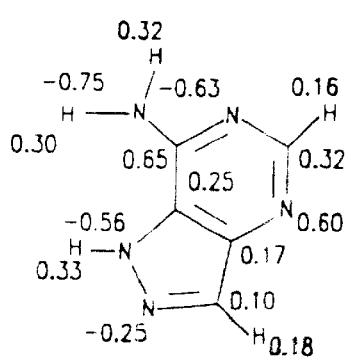
FORMYCIN
Fig. 10A
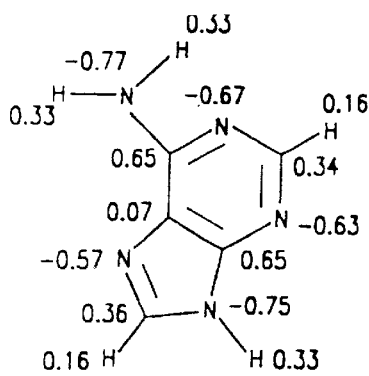
ADENINE(1)
Fig. 10B
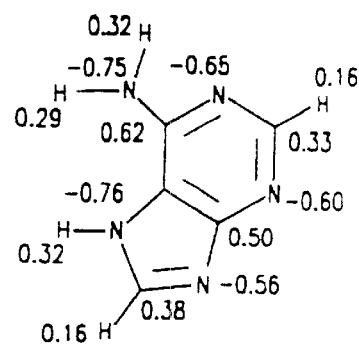
ADENINE(2)
Fig. 10C
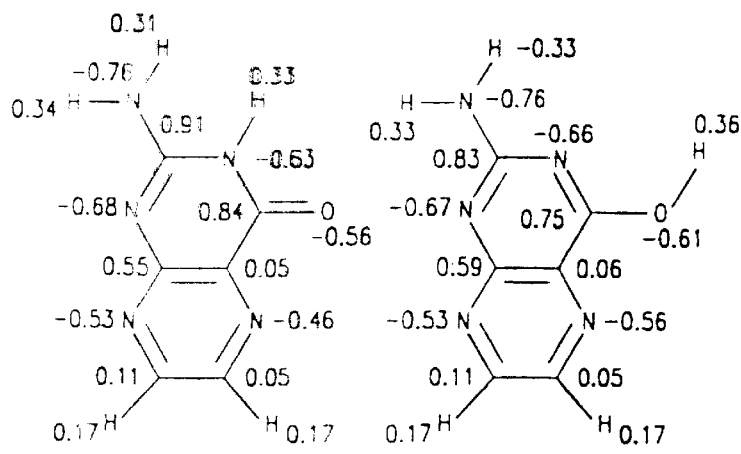
PTERIN(1)
Fig. 10D
PTERIN(2)
Fig. 10E
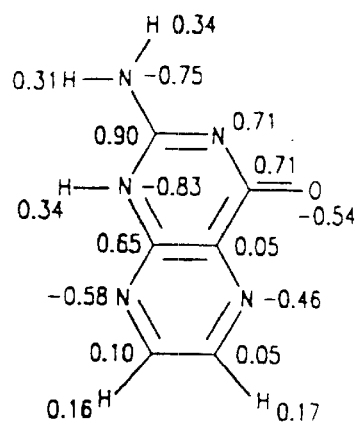
PTERIN(3)
Fig. 10F

PTERIN(4 ION)

GUANINE(1)

GUANINE(2)

GUANINE(3)

GUANINE(4)

2-HYDROXY FORMYCIN 2,4-DIAMINO-PTERIDINE

AHA(ION)

EMODINE

RHODIZONIC ACID

LUMAZINE

S1

S2

S3

| | |
|---|---|
|  2 9 |  1 5 |
| $IC_{50}$ 2.4 mM | $IC_{50}$ 2.8 mM |
|  1 |  2 5 |
| $IC_{50}$ 3.4 mM | $IC_{50}$ 2.7 mM |
|  2 6 |  2 7 |
| $IC_{50}$ 2.5 mM | $IC_{50}$ 3.2 mM |
|  2 8 |  1 4 |
| $IC_{50}$ 0.7 mM | $IC_{50}$ 1.4 mM |
|  2 1 |  2 4 |
| $IC_{50}$ 0.7 mM | $IC_{50}$ 1.4 mM |
|  1 5 |  6 |
| $IC_{50}$ 2.8 mM | $IC_{50}$ 2.1 mM |

RICIN INHIBITORS AND METHODS FOR USE THEREOF

CROSS-REFERENCE TO RELATED APPLICATION

This application is a continuation-in-part of U.S. patent application Ser. No. 09/118,535, filed Jul. 17, 1998, now U.S. Pat. No. 6,177,280 which is a continuation-in-part of U.S. patent application Ser. No. 08/773,398, filed Dec. 24, 1996, abandoned.

FEDERAL FUNDING LEGEND

This invention was supported in part by federal funds, GM 30048 from the National Institutes of Health and by contract number DAMD17-94-C-4006 from the U.S. Army. The U.S. Government may have rights in this invention.

BACKGROUND OF THE INVENTION

1. Field of the Invention

The present invention relates generally to protein chemistry. More specifically, the present invention relates to the identification of inhibitors of the heterodimeric cytotoxin ricin, using computer modeling of the ricin active site as a template in structure-based drug design. Moreover, the present invention relates to the use of the identified inhibitors as antidotes to ricin or to facilitate immunotoxin treatment by controlling non-specific cytotoxicity. In addition, Shiga toxin, a compound essentially identical to the protein originally isolated from *Shigella dysenteriae*, has an active protein chain that is a homologue of the ricin active chain, and catalyzes the same depurination reaction. Thus, the present invention is drawn additionally to identifying inhibitors as antidotes to Shiga toxin.

2. Description of the Related Art

Ricin is a potent he terodimeric cytotoxin easily isolated from the seeds of the castor plant, *Ricinus communis*. The protein consists of a lectin B chain, which can bind cell surfaces and is linked by disulfide bonds to an Achain (RTA), which enzymatically depurinates a key adenine residue in 28 S rRNA (Endo and Tsurugi, *J. Biol. Chem.*, 262:8128–30 (1987)). The molecular structure of ricin is represented in FIGS. 1A and 1B while the adenine depurination reaction mechanism is presented in FIG. 2.

Ricin is an extraordinarily toxic molecule that attacks ribosomes, thereby inhibiting protein synthesis. Ricin has an $LD_{50}$ of approximately 1 μg/kg body weight for mice, rats, and dogs and is ten times more potent against rabbits (Olsnes, S. and Pihl, A., "Toxic Lectins and Related Proteins," *The Molecular Action of Toxins and Viruses*, pp 52–105 (1982)). The toxic dose for humans is likely to be in the μg/kg range which ranks it among the most toxic substances known.

The protein has been used extensively in the design of therapeutic immunotoxins. In these constructs, ricin, RTA, or a related toxin is chemically or genetically linked to an antibody to form a so-called "magic bullet", which can target preferentially those cell lines carrying antigenic markers recognized by the antibody (Frankel, A.E., ed., *Immunotoxins*, Kluwer academic publishers, Boston (1988)).

Ricin also has been used as a poison agent. The protein gained notoriety when it was used in the famous "umbrella tip" assassination of Georgy Markov and was also used in an unsuccessful attempt to poison the Soviet dissident Alexander Solzhenitsyn. More recently, ricin was prepared by a militant anti-tax group which planned to poison IRS personnel.

Given the above, there is interest in identifying or designing potent inhibitors of ricin. These inhibitors could, in principle, be used to facilitate immunotoxin treatment by helping to control nonspecific cytotoxicity, or could be used as antidotes to poison attacks. Recently there has been interest in structure-based drug design—that is, using the knowledge of protein structure to identify enzyme inhibitors. The most common paradigm for this overall process has been called an "iterative protein crystallographic algorithm" by Appelt et al., *J. Med. Chem.* 34:1925–34 (1991), where the design of inhibitors for thymidylate synthetase is described. The main concept of the approach is that the protein active site is used as a template to design or to identify complementary ligands. The identified putative ligands are ranked and tested kinetically. Promising inhibitor candidates are bound to the protein target and analyzed crystallographically for comparison with the proposed model. Additionally, alterations are made in the inhibitor to improve binding and a new round of tests is carried out on the altered compound.

A number of laboratories have used variations on this protocol to design efficacious inhibitors. For example, the search program DOCK (see Kuntz et al., *J. Mol. Biol.* 161:269–88 (1982)) was used to predict that the known anti-psychotic drug haloperidol would bind to the HIV protease (DesJarlais et al., *Proc. Natl. Acad. Sci USA* 87:6644–48 (1990)). Crystallographic studies together with computer aided search methods also were used in the design of inhibitors of purine nucleoside phosphorylase. The program GRID (Goodford, P. J., *J. Med. Chem.* 28:849–57 (1985)) has been used to design two very successful inhibitors of influenza virus. Certain chemical substitutions to the sialic acid substrate were predicted to be energetically favorable, based on interactions with the known X-ray structure of the enzyme. Subsequent binding assays revealed Ki values as low as 0.2 nM. These compounds not only inhibited neuraminidase but retarded viral replication in cultured cell and animal models as well.

The X-ray structure of ricin has been solved (Montfort et al., *J. Biol. Chem.* 262:5398–03 (1987)), refined to 2.5 Å (Rutenber et al., *Proteins* 10:240–50 (1991)), and described in detail (Katzin et al., *Proteins* 10:251–59 (1991); and Rutenber and Robertus, *Proteins* 10:260–69 (1991)). The structure of RTA pressed in *Escherichia coli* has been resolved to 2.3 Å resolution for monoclinic crystals (Mlsna et al., *Prot. Sci.* 2:429–35 (1993)), and recently to 1.8 Å resolution for a tetragonal form (Weston et al., *J. Mol. Biol.* 244:410–422 (1994)).

The X-ray model of RTA allowed identification of a number of amino acids which were hypothesized to be important for substrate binding and for the depurination mechanism; these residues include Glu 177, Arg 180, Trp 211, Tyr 80 and Tyr 123. Site-directed mutagenesis of the cloned RTA gene has been used to examine the relative significance of these residues (see, e.g., Schlossman et al., *Mol. Cell. Biol.* 9:5012–21 (1989); Frankel et al., *Mol. Cell. Biol.* 10:6257–63 (1990); Ready et al., *Proteins* 10:270–78 (1991); and Kim and Robertus, *Protein Engineering* 5:775–79 (1992)). In addition, Monzingo and Robertus, *J. Mol. Biol.* 227:1136–45 (1992), carried out an X-ray analysis of substrate analogs in the RTA active site, examining FMP, adenyl guanosine (ApG) and guanyl adenosine (GpA). The structure of important substrate and analog bases, together with the numbering scheme used in energy minimizations, is shown in FIGS. 8A–8D.

Several closely related mechanisms of action have been proposed which incorporate elements of both the structural and kinetic analyses. It is likely that the susceptible adenine base binds between tyrosines 80 and 123 while forming specific hydrogen bonds with the backbone carbonyl and amido nitrogen of Val 81 and with the carbonyl of Gly 121. In the hydrolysis, the leaving adenine is at least partially protonated by Arg 180, and Glu 177 may stabilize a putative oxycarbonium transition state or, more likely, act as a base to polarize the attacking water.

Shiga toxin, a compound essentially identical to the protein originally isolated from *Shigella dysenteriae*, has an A chain which is activated by proteolysis, generating an active A1 enzyme and an A2 fragment, which remains bound until a disulfide bond linking them is reduced. The active A1 chain (STA1) is a homologue of RTA, and catalyzes the same depurination reaction. *E. coli* strains can carry the gene for Shiga toxin, and this renders them pathogenic. Human infection by Shiga toxin lead to hemorrhagic colitis and hemolytic-uremic syndrome—commonly referred to as "hamburger disease"—a severe and often fatal form of food poisoning. It is difficult to control outbreaks of hamburger disease because antibiotics tend to lyse the bacteria, releasing the destructive toxin into the system, aggravating tissue damage and internal bleeding. An effective inhibitor of STA1 would be a powerful adjunct to treatment of hemorrhagic colitis and hemolytic-uremic syndrome.

The Shiga toxin gene has been cloned and engineered to express the enzyme. A comparison of the amino acid sequences of RTA and STA show clearly that they are homologues. An energy-minimized model of STA1 was constructed (Deresiewicz et al, *Biochemistry* 31:3272–80 (1992)), and it was noted that key residues conserved among plant Ribosome Inactivating Protein (RIP) enzymes are conserved in STA1 (Katzin et al., *Proteins* 10:251–59 (1991)).

Until the present invention, no inhibitors for RTA or STA1 had been identified. Even FMP, which is known to bind RTA, is not an effective inhibitor of the RTA. Thus, the prior art is deficient in identifying compounds which are effective inhibitors of ricin. The present invention fulfills this long-standing need and desire in the art.

SUMMARY OF THE INVENTION

The present invention provides compounds that are effective inhibitors of the cytotoxic proteins ricin or Shiga toxin.

In one object of the present invention, there is provided a compound effective for inhibiting ricin, the compound able to act within an active site of RTA and having an aromatic heterocyclic molecular core, wherein the aromatic heterocyclic molecular core resembles an adenine moiety in size and shape and is derivatized with at least one polar substituent such that the polar substituent interacts in the active site of RTA. In another embodiment of this object of the invention there is provided a compound wherein said polar substituent is an amine group able to donate hydrogen bonds to a carbonyl oxygen of Val 81 or Gly 121. As another embodiment of this object of the present invention, there is provided a compound wherein the inhibitor further comprises at least one pendant group which binds an amino acid adjacent to the active site. In addition, the inhibitor further may comprise at least one moiety which reacts with a shallow channel in the RTA chain.

In another object of the present invention, there is provided a compound effective for inhibiting ricin, the compound being able to act within an active site of RTA, having nonpolar interactions with a side chain of an amino acid in the active site selected from the group Tyr 80, Ile 172 or Tyr 123, and having polar interactions with a side chain of an amino acid in the active site, selected from the group of carbonyl oxygens; of Gly 121 or Val 81, backbone amides of Val 81 or Tyr 123, or atoms on side chains of Arg 180, Tyr 80, Tyr 123 or Asn 78. In addition, an embodiment of the present object provides an inhibitor further comprising at least one nonpolar moiety which interacts with side chains from Trp 211, Leu 45, Val 256, Tyr 257 or Thr 77 of said RTA chain. Alternatively, the inhibitor may possess at least one polar moiety which interacts with the carbonyl oxygens of Thr 77 or Tyr 257, or side chains from Asn 47 and Arg 258 of the RTA chain, or further comprise at least one polar moiety which interacts with an amino acid from a second pocket of said RTA chain. In addition, the inhibitor may interact in a nonpolar fashion with side chains from amino acids selected from the group of Tyr 80, Val 82, Phe 57, Thr 77 and Arg 56.

In yet another object of the present invention, there is provided a compound effective for inhibiting ricin, wherein said compound is a pteroic acid analog.

In an additional object of the present invention, there is provided a compound effective for inhibiting Shiga toxin, the compound able to act within an active site of STA1 and having an aromatic heterocyclic molecular core, wherein the aromatic heterocyclic molecular core resembles an adenine moiety in size and shape and is derivatized with polar substituents such that the polar substituents interact in the active site of RTA.

An additional object of the present invention, there is provided a compound effective for inhibiting Shiga toxin, wherein said compound is a pteroic acid analog.

Additionally, the present invention provides a method for identifying a compounds effective for inhibiting ricin, comprising the steps of performing at least one technique from the group of molecular modeling, crystallography, and energy minimization; protein synthesis assay; and phage display, and a method for identifying a compounds effective for inhibiting Shiga toxin, comprising the steps of performing at least one technique from the group of molecular modeling, crystallography, and energy minimization; protein synthesis assay; and phage display.

Another object of the present invention is to provide the pteroic acid analog as a pharmaceutical compound as an antidote to ricin or to facilitate immunotoxin treatment by controlling non-specific cytotoxicity.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 1A shows the entire ricin protein. The A chain is in the upper right and the B chain is at the lower left. The two lactose moieties are represented as pairs of discs bound to the B chain. The chains have been separated to facilitate viewing. The disulfide bond linking the chains is indicated in the lower right portion of the molecule. The A chain has been divided into three domains as follows: residues 1–117 shown in small dot pattern, residues 118–210 shown as open ribbon, and residues 211–267 shown in large dot pattern. FIG. 1B shows a close up representation of the ricin A chain.

FIG. 22A shows the method of synthesis of 4-[(2-amino-4-oxo-4,7-dihydro-3H-pyrrolo[2,3-d]pyrimidin-5-ylmethyl)-amino]-benzoic acid 21. The synthesis of 2-amino-5-{[4-(4-amino-benzyl)-phenylamino]-methyl}-3,7-dihydro-pyrrolo[2,3-d]pyrimidin-4-one 24 used the same method except that octanoic acid{5-[(dibenzylamino)-methyl]-4-oxo-4,7-dihydro-3H-pyrrolo[2,3-d]pyrimidin-2-yl}-amide 18 is reacted with 4-amino-methylbenzoate 19 instead of 4-[(2-octanoylamino-4-oxo-4,7-dihydro-3H-pyrrolo[2,3-d]pyrimidin-5-ylmethyl)-amino]-benzoic acid methyl ester 20. This altered step is shown in FIG. 22B.

DETAILED DESCRIPTION OF THE INVENTION

Figure 1A:
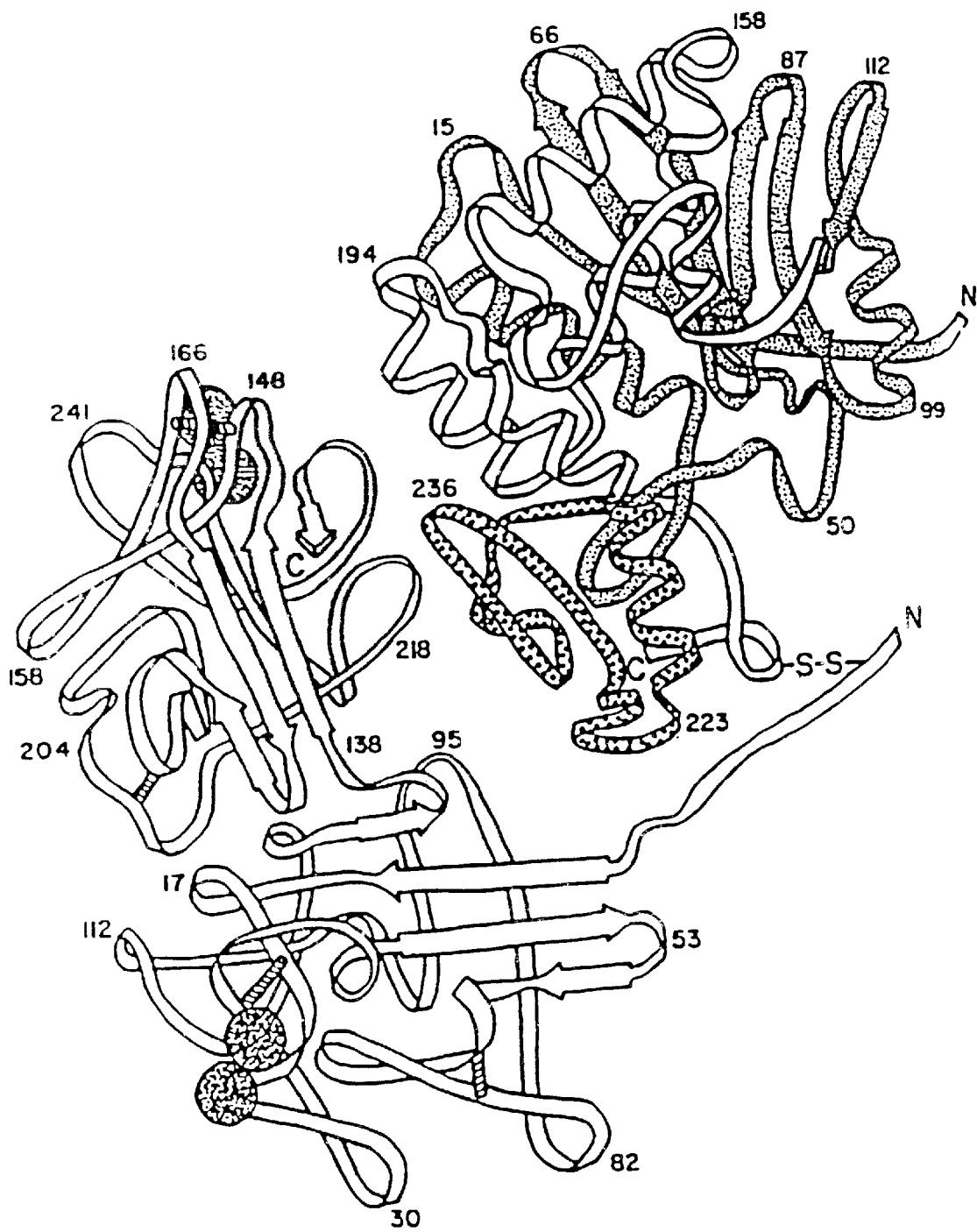
FIGS. 1A and 1B shows a ribbon representation of the ricin backbone.

As used herein, the term "ricin" refers to a heterodimeric cytotoxic protein isolated from *Ricinus communis*, or a protein expressed in a heterologous system from the ricin gene. Ricin contains a lectin B chain (RTB) and an N-glycosidase A chain (RTA).

As used herein, the term "RTA substrate specificity pocket" refers to the portion of the RTA active site that binds adenine. The term "RTA active site" refers to that portion of RTA which binds the rRNA substrate. The active site is large, generally polar, and interacts with the highly charged rRNA. The purine ring of the rRNA adenine rests between the side chains of tyrosines 80 and 123, and four polar protein groups in the active site (O121, O81, NH81 and NH1 of Arg 180) make hydrogen bonds with the substrate.

As used herein, the term "secondary pocket" refers to the portion of the RTA molecule that is a fairly large and generally nonpolar cavity of the opposite side of Tyr 80 from the adenine-binding site.

As used herein, the term "shallow channel" refers to the portion of the RTA molecule that forms a sort of rut, runs from the specificity pocket along its surface, and is flanked by Arg residues (213, 258, 48 and 56, moving away from the catalytic site).

As used herein, the term "inhibitor" refers to a small molecule which binds to RTA and retards its enzyme action.

As used herein the term "immunotoxin" refers to refers to a chemical or genetic linkage between an antibody with a binding preference for a target cell type, and a toxic protein such as ricin or RTA.

As used herein the term "non-specific cytotoxicity" refers to the intoxication of cells which are not targeted by an immunotoxin.

As used herein the term "pteroic acid" or "PTA" refers to 4-[[(2-amino-1,4-dihydro-4-oxo-6-teridinyl)methyl]amino]benzoic acid.

As used herein, the term "formycin monophosphate" or "FMP" refers to an AMP analog in which the adenine ring is replaced by a pyrazolopyrimidine ring (that is, the N9 of adenine is replaced by C and C8 is replaced by N).

As used herein, the term "neopterin" refers to 2-amino-6-(1,2,3-trihydroxypropyl)-4(3H)-pteridone.

As used herein, the term "guanine (4) tautomer" refers to the guanine tautomer in which hydrogen is bonded to N3 and not to N1.

As used herein, the term "inhibitor design" refers to a process of identifying inhibitors or improving the properties of a known inhibitor.

As used herein, the term "molecular modeling" or "computer modeling" refers to fitting a model ligand compound, such as an inhibitor candidate, into the active site space of a protein model and adjusting the models according to chemical principles to simulate their interactions; this is usually done with a computer display system.

As used herein, the term "X-ray structure" refers to a model of a protein or protein•ligand complex which is based on experimental data obtained by X-ray diffraction from crystals of the protein or complex).

As used herein, the term "SYBYL" refers to a computer program distributed by TRIPOS Corporation which can be used to model proteins or complexes, and also can be used to calculate the energy of interaction between atoms or groups, based on various approximations of chemical laws.

As used herein, the term "6–31 g** basis set" refers to a mathematical function used by the program SYBYL to approximate the distribution of electrons within atomic orbitals.

As used herein, the term "X-PLOR" refers to a suite of computer programs written by Axel Brunger and used routinely to adjust models to their lowest energy state, consistent with the observed experimental X-ray diffraction data.

As used herein, the term "energy minimization" refers to adjusting the atoms or chemical groups within a model so that the new model assumes the lowest energy—that is, the most likely conformation of the model, based on approximations to chemical laws.

As used herein the term "OMIT" refers to a kind o f electron density map based on the observed X-ray amplitude data for a protein and phases calculated from a partial model.

As used herein the term "$F_o$–$F_c$" refers to the coefficients used to compute a kind of electron density map commonly called a "difference Fourier", and used to show those parts of a protein or complex which have changed as a result of some action, such as, but not limited to, inserting a ligand.

Ricin is a potent cytotoxin which has been used widely in the construction of therapeutic agents such as immunotoxins. Recently it has been used by governments and underground groups as a poison. There is interest in identifying and designing effective inhibitors of the ricin A chain (RTA). The present invention utilizes computer-assisted searches to identify compounds that bind in the RTA active site, which normally recognizes a specific adenine base on rRNA. Kinetic assays indicated that pteroic acid (PTA) could inhibit RTA activity with an apparent Ki of 0.6 mM, and a 2.3 Å crystal structure of the complex revealed the mode of binding. In the same way that PTA was identified as an inhibitor, other compounds have been assayed in the method of the present invention. The present invention is directed to compounds that are effective inhibitors of the cytotoxic protein ricin and methods for screening for additional inhibitors.

In addition, a molecular model of STA1 based on RTA has been proposed. The X-ray structure of the Shiga toxin B chain has been solved, as has the intact $(A1A2)B_5$ toxin, which showed that the proposed model was sound. Respective matching of the RTA and STA1 active site finds Arg 180, the key catalytic residue in RTA, corresponds to Arg 170 in STA1, Glu 177 with Glu 167, Tyr 80 with Tyr 77, Tyr 123 with Tyr 114, and Trp 211 with Trp 207. The X-ray structure of the Shiga toxin holotoxin $(A1A2B_5)$ has been solved (Fraser, et al., *Nature Struc. Biol.* 1:59–69 (1994), confirming the general similarity of RTA and STA1.

Thus, the present invention provides a method of screening for a ricin inhibitor, comprising the steps of: identifying a test compound, wherein said test compound binds to the active site of the ricin A chain, has an aromatic heterocyclic molecular core resembling an adenine moiety in size and shape and is derivatized with polar substituents; and measuring the ability of said test compound to displace binding of a second compound known to bind to the active site of the ricin A chain, wherein said second compound is selected from the group of pteroic acid, pteroic acid analogs, neopterin, pterin (3) tautomer, guanine (4) tautomer, 4-[(2-amino-4-oxo-4,7-dihydro-3H-pyrrolo[2,3-d]pyrimidin-5-ylmethyl)-amino]-benzoic acid 21, and 2-amino-3,7-dihydro-pyrrolo[2,3-d]pyrimidin-4-one 15 wherein a competitive displacement of said second compound by the test compound indicates that the test compound is a ricin inhibitor. Preferably, the test compound acts within the active site of ricin A chain, has nonpolar interactions with a side chain of an amino acid in said active site selected from the group Tyr 80, Ile 172 or Tyr 123, and has polar interactions with a side chain of an amino acid in the active site selected from the group of carbonyl oxygens of Gly 121 or Val 81, backbone amides of Val 81 or Tyr 123 and atoms on side chains of Arg 180, Tyr 80, Tyr 123 or Asn 78. The test compound may further comprise at least one nonpolar moiety which interacts with side chains from Trp 211, Leu 45, Val 256, Tyr 257 or Thr 77 of said RTA chain. The test compound may further comprise at least one polar moiety which interacts with the carbonyl oxygens of Thr 77 or Tyr 257, or side chains from Asn 47 and Arg 258 of said RTA chain. The test compound may further comprise at least one polar moiety which interacts with an amino acid from a second pocket of said RTA chain. Preferably, the identifying occurs by a technique selected from the group consisting of molecular modeling, crystallography, energy minimization protein synthesis assay and phage display.

The present invention also provides a method of screening for a Shiga toxin inhibitor, comprising the steps of: identifying a test compound, wherein said test compound acts within an active site of Shiga toxin A chain, has an aromatic heterocyclic molecular core resembling an adenine moiety in size and shape and is derivatized with polar substituents such that said polar substituents interact in said active site of Shiga toxin A chain; and measuring the ability of said test compound to displace binding of a second compound known to bind to the active site of the Shiga toxin, wherein said second compound is selected from the group of pteroic acid, pteroic acid analogs, neopterin, pterin (3) tautomer, guanine (4) tautomer, 4-[(2-amino-4-oxo-4,7-dihydro-3H-pyrrolo[2, 3-d]pyrimidin-5-ylmethyl)-amino]-benzoic acid 21 and 2-amino-3,7-dihydro-pyrrolo[2,3-d]pyrimidin-4-one 15, wherein a competitive displacement of said second compound by the test compound indicates that the test compound is a Shiga toxin inhibitor. Preferably, the identifying occurs by a technique selected from the group consisting of molecular modeling, crystallography, energy minimization protein synthesis assay and phage display.

The present invention is also directed to a compound effective for inhibiting ricin, said compound able to act within an active site of RTA and having an aromatic heterocyclic molecular core, wherein said aromatic heterocyclic molecular core resembles an adenine moiety in size and shape and is derivatized with polar substituents such that said polar substituents interact in said active site of RTA. In one aspect, the polar substituent is an amine group able to donate hydrogen bonds to a carbonyl oxygen of Val 81 or Gly 121. In another aspect, inhibitor further comprises at least one pendant group which binds an amino acid adjacent to said active site. The inhibitor may further comprise at least one moiety which reacts with a shallow channel in said RTA chain.

The present invention is also directed to a compound effective for inhibiting ricin, said compound being able to act within an active site of RTA, having nonpolar interactions with a side chain of an amino acid in said active site selected from the group Tyr 80, Ile 172 or Tyr 123, and having polar interactions with a side chain of an amino acid in said active site selected from the group of carbonyl oxygens of Gly 121 or Val 81, backbone amides of Val 81 or Tyr 123, or atoms on side chains of Arg 180, Tyr 80, Tyr 123 or Asn 78. The inhibitor may further comprise at least one nonpolar moiety which interacts with side chains from Trp 211, Leu 45, Val 256, Tyr 257 or Thr 77 of said RTA Chain. The inhibitor may further comprise at least one polar moiety which interacts with the carbonyl oxygens of Thr 77 or Tyr 257, or side chains from Asn 47 and Arg 258 of said RTA chain. The inhibitor may further comprise at least one polar moiety which interacts with an amino acid from a second pocket of said RTA chain. In one aspect, the inhibitor may interact in a nonpolar fashion with side chains from amino acids selected from the group of Tyr 80, Val 82, Phe 57, Thr 77 and Arg 56. The compound may be a pteroic acid analog such as 4-[(2-amino-4-oxo-4,7-dihydro-3H-pyrrolo [2,3-d]pyrimidin-5-ylmethyl)-amino]-benzoic acid 21. Representative examples of ricin inhibitor compounds include 2,6-diamino-3H-pyrimidin-4-one 1,2-amino-6-dihydroxy-5-methylpyrimidin-4-one 25, 2-amino-6-methylpyrimidin-4-one 26, 6-amino-2-methyl-3H-pyrimidin-4-one 27, 2-amino-8-mercapto-1,9-dihydro-purin-6-one 28, 2,5-diamino-6H-thiazolo[4,5-d]pyrimidin-7-one 14 4-[(2-amino-4-oxo-4,7-dihydro-3H-pyrrolo[2,3-d]pyrimidin-5-ylmethyl)-amino]-benzoic acid 21, 2-amino-5- {[4-(4-amino-benzyl)-phenylamino]-methyl }-3,7-dihydro-pyrrolo [2,3-d]pyrimidin-4-one 24 and 2-amino-6-methyl-3,7-dihydro-pyrrolo[2,3-d]pyrimidin-4-one 6.

The present invention is also directed to a compound effective for inhibiting Shiga toxin, said compound able to act within an active site of STA1 and having an aromatic heterocyclic molecular core, wherein said aromatic heterocyclic molecular core resembles an adenine moiety in size and shape and is derivatized with polar substituents such that said polar substituents interact in said active site of RTA. In one aspect, the compound is a pteroic acid analog. A representative example of such an analog is 2-amino-5-[(4'-benzoyl)methylamino]-3,4-dihydro-4-oxo-7H-pyrrolo [2,3d]-pyrimidine.

The following examples are given for the purpose of illustrating various embodiments of the invention and are not meant to limit the present invention in any fashion.

EXAMPLE 1

Preparation Of Recombinant RTA And Protein Synthesis Assay

Recombinant RTA was prepared as described by Ready et al., *Proteins* 10:270–78 (1991). Recombinant RTA was prepared as described by Chaddock and Roberts, *Protein Engineering* 6:425–31 (1993). Briefly, 50 ml cultures of *E. coli* JM101 harboring plasmid pUTA (Ready. et al, *Proteins* 10:270–78 (1991)) was grown overnight at 37° C., then used to inoculate 500 ml 2YT media and grown for 2 hours at 30° C. Expression of RTA was induced by addition of 50 $\mu$l 0.5M isopropyl-1-thio-β-galactoside (IPTG) and incubation for 4 hours at 30° C. Cells were harvested by centrifugation, resuspended in 30 ml 5 mM sodium phosphate (pH 6.5), and broken with a French pressure cell. Following centrifugation to remove cell debris, the supernatant was loaded onto a 100 ml carboxymethyl-sepharose (Pharmacia) column equilibrated in the same buffer. Unbound protein was washed from the column with 1500 ml buffer followed by 200 ml buffer containing 100 mM sodium chloride. RTA was eluted with a linear 500 ml 0.1–0.3 M sodium chloride gradient. Peak RTA-containing fractions were pooled and stored at 4° C. at approximately1 mg/ml. Typical yields were 40–50 mg RTA/1 media for wild type RTA.

RTA activity was measured by its ability to inhibit protein synthesis in an in vitro protein synthesis assay using *Artemia salinas* ribosomes, as described previously by Ready et al, Biochem. Biophys. Acta 740:19–28 (1983) and Ready et al, *Proteins* 10:270–78 (1991). Thirty-four pmoles of *Artemia salinas* ribosomes were incubated in a volume of 120 $\mu$l for 5 minutes at 25° C. with inhibitor (pteroic acid) ranging in concentration from 0.062 mM to 1.67 mM, with or without 1.5 mM spermine. The reaction was stopped by the addition of 400 nmoles of anti-RTA antibody. 100 ml of a protein synthesis mix containing $^{14}$C-Phe and wheat germ extract was added to all the tubes. After a 15 minute incubation at 25° C., the reaction was stopped by the addition of 5% TCA. The mixture was heated to 90° C. for 10 minutes, then passed through a Millipore nitrocellulose filter. The filters were dried and counted by liquid scintillation counting. Inhibitor candidates were judged by their ability to disrupt RTA action against the *Artemia ribosomes.*

Pterin compounds including pterin-6 carboxylic acid, neopterin, pteroic acid, and folic acid were purchased from Sigma Chemical Company (St. Louis). Concentrations were evaluated spectroscopically, assuming the same ultraviolet spectrum as folic acid, that is $e_{283}$=25,000. Because of the limited solubility of the pterins, the ribosome inhibition assays and controls were carried out at pH 9.

EXAMPLE 2

Crystallography And Molecular Modeling

Crystals of RTA were grown in the monoclinic form (see Robertus et al., *J. Biol. Chem.* 262:19–20 (1987); and Mlsna et al., *Prot. Sci.* 2:429–35 (1993)) or in a tetragonal form (Weston et al., *J. Mol. Biol.* 244:410–22 (1994)). Three-dimensional diffraction data were collected on a San Diego Multiwire Systems area detector. (see Hamlin, *Methods in Enzymology* 114:416–52 (1985)) with a Rigaku RU-200 X-ray source operating at 50 kV, 110 mA with a graphite monochromator. Data was collected using the method of Xuong et al., *J. Appl. Cryst.* 18:342–50 (1985), and reduced and evaluated using the University of California, San Diego (UCSD) software system (Howard et al., *Methods in Enzymology* 114:453–72 (1985)). Rotation and translation searches, as well as crystallographic refinement of the RTA inhibitor, complex (energy minimization and simulated annealing), were carried out using the X-PLOR package (Brünger, Crystallographic refinement by simulated annealing, *Crystallographic Computing 4: Techniques and New Technologies*, Oxford: Clarendon Press, pp. 126–140. (1988)). Molecular modeling was carried out using FRODO (see Jones, *FRODO: A graphics fitting program for macromolecules, Computational Crystallography*, Oxford: Oxford University Press, pp. 303–317 (1982)), running on an Evans and Sutherland PS390.

Molecular modeling programs CHEMX and SYBYL were purchased from Chemical Design Ltd. (Oxon, England) and Tripos Inc. (St. Louis) respectively. Interaction energies were calculated, with the Tripos force field. The energy minimization was terminated when a 0.05 energy gradient value was reached using the Powell algorithm as implemented in SYBYL. A distance dependent and a constant function (dielectric constant=1.5) were used for dielectric effects, with the expectation that the distance dependent function can simulate the internal protein dielectric, while the constant function simulates the solvent effect on the protein. Non-bonded cutoff was 8.0 C. The net atomic charges used in minimization were from the Kollman method (Weiner et al., *J. Am. Chem. Soc.*, 106:765–84 (1984)) for RTA and from ab initio calculation (6–31 g** basis set) for ligands; these were calculated on CRAY YMP and COIL located at the National Institutes of Health.

EXAMPLE 3

Energy Minimization

According to the ab initio minimization, the hybridization of an amino N atom connected to an aromatic ring is variable depending on its environment. Table 1 lists the deviation from the ring plane of two hydrogens on such N atoms. It shows that some N atoms are sp2 types, and some are combinations of sp2 and sp3 types. If the deviation sum from the aromatic plane is larger than 30 degrees, the N atom was dealt with as sp3 type in the molecular mechanics calculation.

TABLE 1

The deviation sum (degree) of hydrogens of amino N atom from aromatic ring plane according to ab initio (6–31 g**) minimization

| structure | deviation |
|---|---|
| formycin | 41.1 |
| adenine(1) | 0.7 |
| adenine(2) | 44.0 |
| Pterin(1) | 37.1 |
| pterin(2) | 0.8 |
| pterin(3) | 36.9 |
| pterin(4 ion) | 0.1 |
| guanine(1) | 38.1 |
| guanine(2) | 27.8 |
| guanine(3) | 32.1 |
| guanine(4) | 41.3 |
| 2,4-diamino-pteridine | * |
| 3-Amino-4-hydroxybenzoic acid (ion) | 55.7 |
| S2(ion) | 0.0 |

*Two amino N atoms, on which all hydrogens are in the aromatic ring plane.

In the energy minimization protocol, the energies for the crystal complexes of ricin with FMP (Monzingo, and Robertus, *J. Mol. Biol.* 227:1136–45 (1992)) and pteroic acid were minimized first. Next, these structures were reminimized after FMP and pteroic acid were replaced by formycin and pterin. Then the formycin or pterin was replaced by other structures one by one. The newly-formed complexes also were fully minimized by the criteria mentioned above for obtaining the interaction energies between ricin and ligands. The interaction energy was obtained by subtracting the unliganded ricin energy and ligand energy (in its binding conformation) from the complex energy. Some of the structures studied were small and not very different from formycin, adenine or pterin. It was assumed that these small structures causes only small changes in the RTA conformation and there is no requirement to perform molecular dynamics simulation for conformation searching.

EXAMPLE 4

Identification of Pteroic Acid as an Inhibitor

A query was constructed using the geometric and bonding parameters of the observed FMP ligand, and a search of the NCI data base was made with CHEMX. Among the compounds predicted to have hydrogen bond donors and acceptors in an orientation favorable for RTA interaction was the pterin derivative called pteroic acid (PTA). SYBYL calculations suggested that PTA might bind better than FMP. Interaction enthalpies, calculated assuming one negative charge on each ligand, were −106 Kcal/mole for pteroic acid, as compared with −89 Kcal/mole for FMP. It is important to note that the interaction enthalpies do not consider such terms as configurational entropy nor the effect of solvent interactions, and thus are not meant to represent the free energy of binding the ligand to the protein. Rather, the calculation is intended to serve as a rough guide to comparing the likely affinities of related compounds for the target enzyme.

Figure 3A:
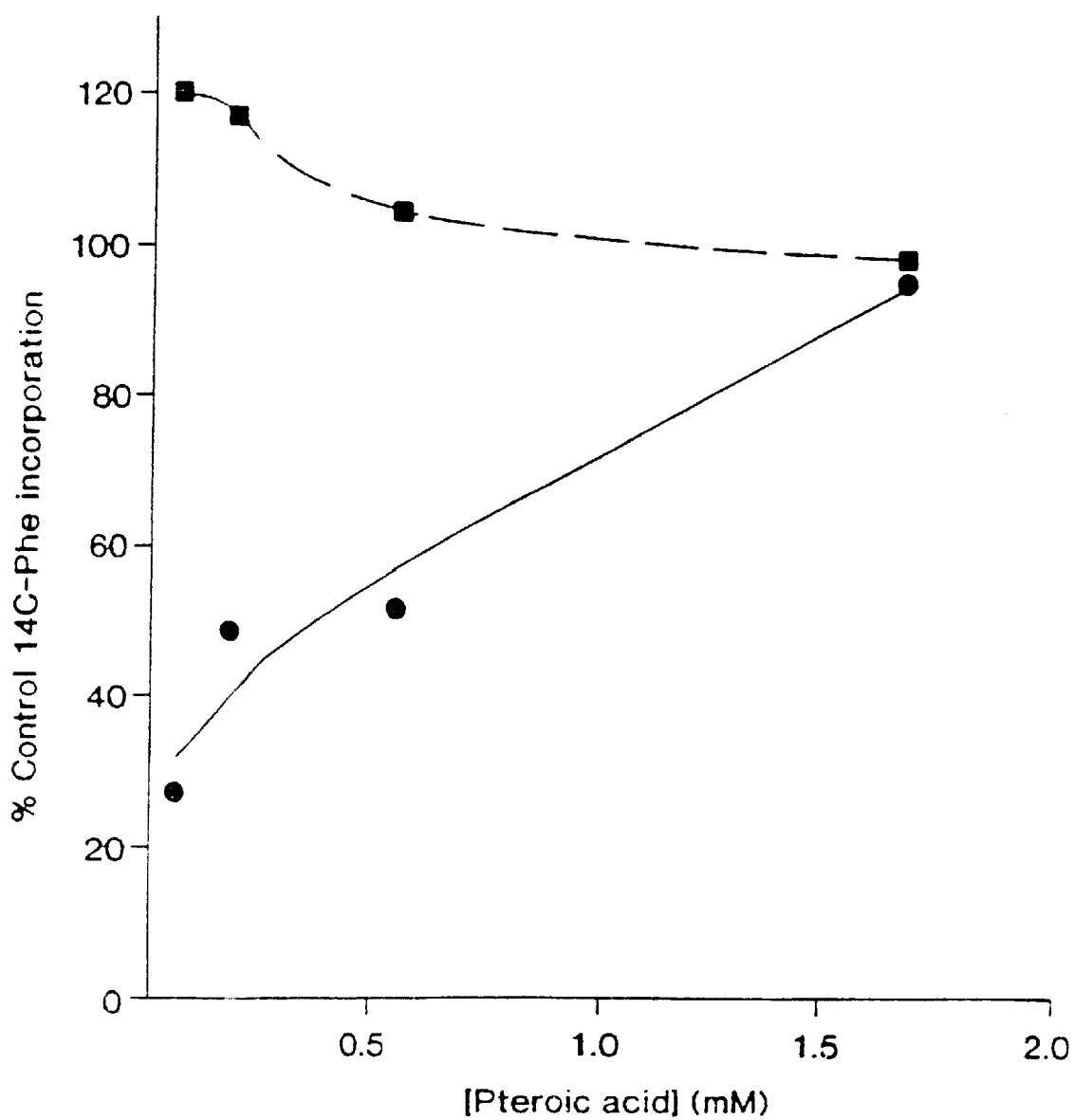
FIGS. 3A and 3B show the inhibition of ricin A chain (RTA) by pteroic acid. Pteroic acid (squares) has a minor inhibitory effect on the protein synthesis using *Artemia salinas* ribosomes. Protein synthesis is reduced to about 20% in the presence of 1.5 nM RTA (circles) but toxin action is inhibited by increasing doses of pteroic acid. The inset replots the level of RTA activity as a function pteroic acid concentration.
Figure 3B:
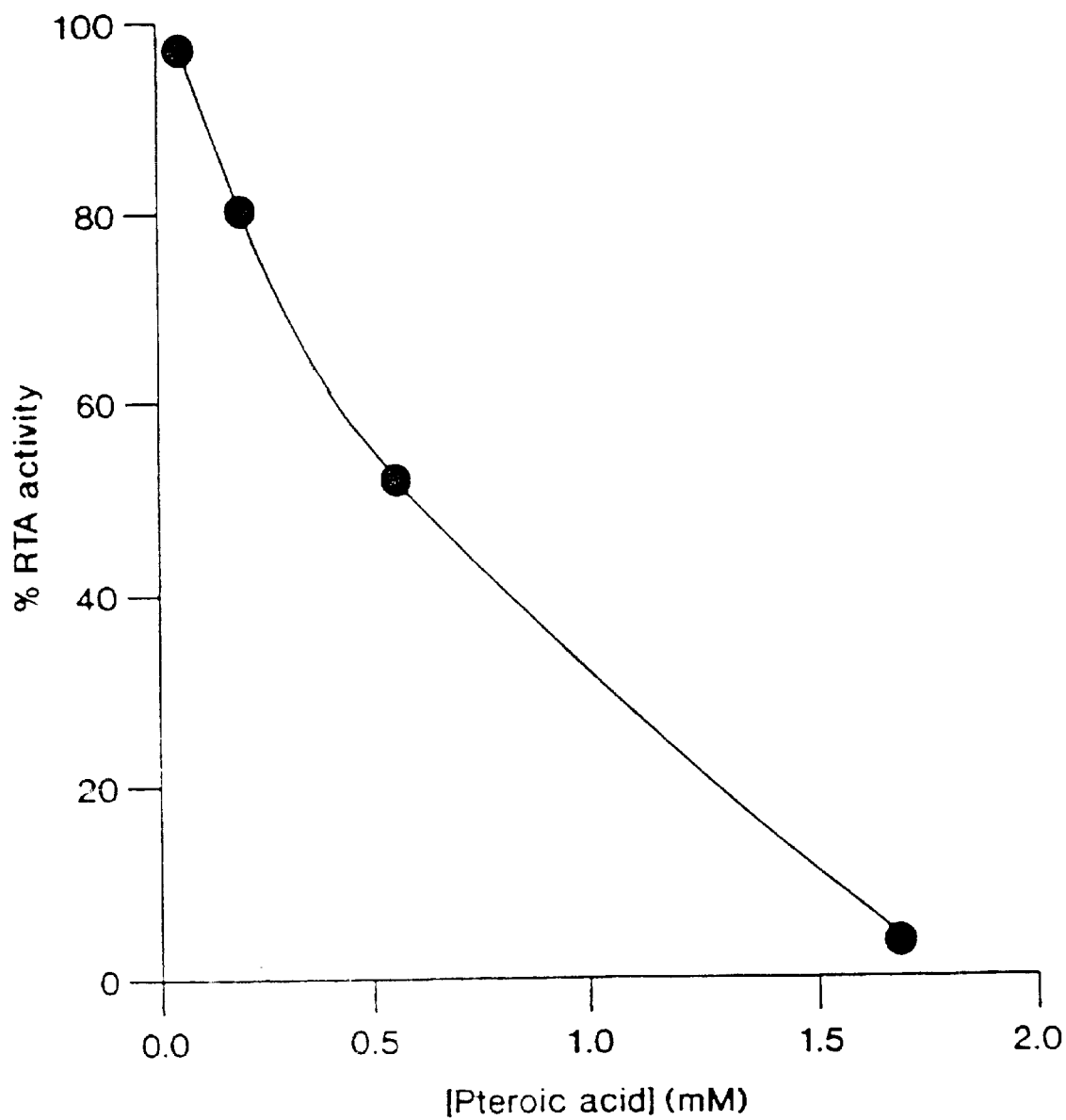

To determine if pteroic acid was indeed an inhibitor of RTA, it was tested in the protein synthesis assay; because of the limited solubility of PTA, the experiments and controls were carried out at pH9. FIGS. 3A and 3B show protein synthesis on 300 nM *Artemia ribosomes* in the presence of varying concentrations of pteroic acid, and in the presence or absence of 1.5 nM RTA. The figures show that pteroic acid has a minor inhibitory effect on protein synthesis itself—a 1.7 mM concentration of pteroic acid inhibits protein synthesis about 20%. The inset panel replots the data as the fraction of possible RTA activity versus the concentration of pteroic acid. It shows that 0.6 mM pteroic acid reduces RTA action by 50% and defines the effective Ki for the inhibitor.

Several efforts were made to observe crystallographically the binding of pteroic acid to RTA. The strongly diffracting tetragonal crystals are grown at pH 4.5 and would not bind the inhibitor either when soaked in a saturated solution or when cocrystallized. However, monoclinic crystals at pH 9 were made 20% saturated with pteroic acid and soaked for seven days. Although the crystals cracked initially, over the soaking time most of the cracks annealed. Diffraction showed that the complex was not isomorphous with the native. Native cell parameters are a=42.6, b=68.1, c=50.2 Å and β=112.9° (Robertus et al., *J. Biol. Chem.* 262:19–20 (1987)). The pteroic acid complex crystals have the following parameters: a=39.0, b=64.4, c=49.4 Å and β=108.0°.

Three dimensional data were collected to 2.3 Å including 68,262 observations of 10,999 reflections; reflection intensities scaled with R=6.5%. Since the crystals were not isomorphous with the native, the RTA•PTA complex was solved using molecular replacement methods. The monoclinic RTA was used as a model for a rotation search using the program X-PLOR. Data between 10 and 4 Å showed no rotation. A translation search was then executed with X-PLOR. The translation search revealed a translation of 0.65 Å along x, and of 2.82 Å along z. The initial positioning was completed using the rigid body refinement option of X-PLOR; the R factor to 3 Å resolution was 0.36.

Figure 4B:
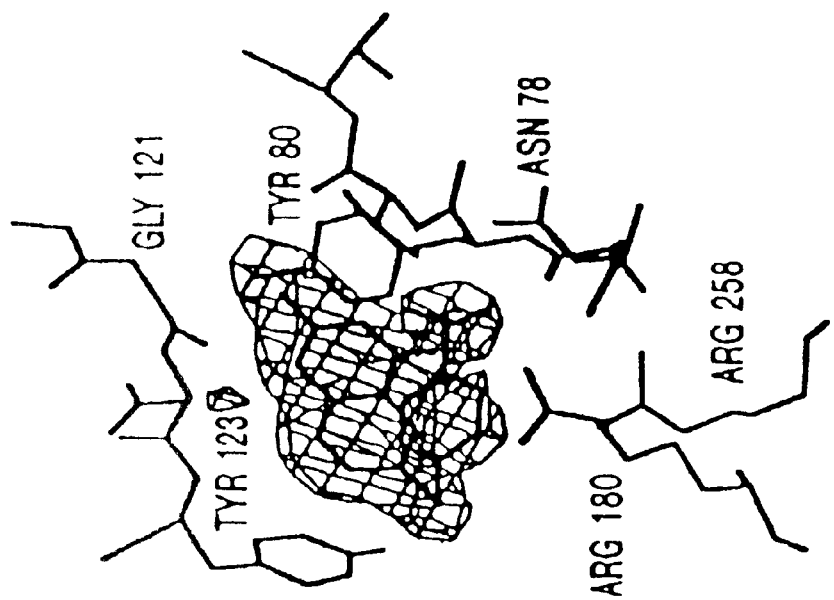
FIGS. 4A and 4B show the electron density for pteroic acid complexed to RTA. This is OMIT density based on Fo-Fc coefficients and phases from the protein model in which Tyr 80 has been displaced to form the normal substrate-binding site. The difference density baskets are contoured at the 3s level. The refined position of PTA is shown superimposed on the difference density.
Figure 4A:
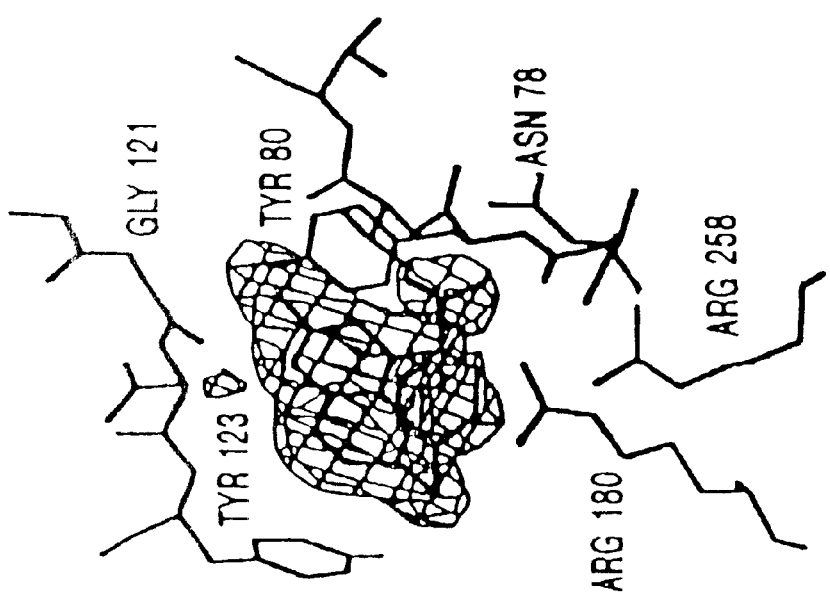

A difference map with coefficients (Fo-Fc) was calculated and showed a mixture of positive and negative peaks within the active site. These peaks could be interpreted as the binding of PTA in the area previously seen to bind FMP. The pterin ring occupies the same site as the formycin ring of FMP or the adenine ring of the ApG dinucleotide. This requires that the Tyr 80 side chain rotate roughly 45° to stack with the aromatic surface of the pterin, in a way similar to that seen for FMP (see Monzingo and Robertus, *J. Mol. Biol.* 227:1136–45 (1992)). The Tyr 80 position in the model was adjusted and a second (Fo-Fc) map computed. This OMIT map is shown in FIGS. 4A and 4B. There is clear electron density for the pterin moiety of the inhibitor; the benzoic acid density is weaker but still allows that group to be readily positioned. PTA was built into the density and the model subjected to four successive rounds of energy minimization and simulated annealing using X-PLOR. Between each round of refinement, the resolution was increased by 0.2 Å beginning at 3.0 Å and ending at 2.3 Å. Another difference map was calculated and 45 waters were added to the structure. After a final round of energy minimization and isotropic temperature factor refinement, a final R-factor of 17.9% was calculated for all data to 2.3 Å. Isotropic temperature factor refinement showed the pterin ring, with average B values of 11, was more rigidly held than the benzoic acid moiety where average B values were 26. The occupancy of the pteroic acid refined to 1.0, as compared to 0.5 seen previously for FMP (see Monzingo and Robertus, *J. Mol. Biol.* 227:1136–45 (1992)).

Figure 5:
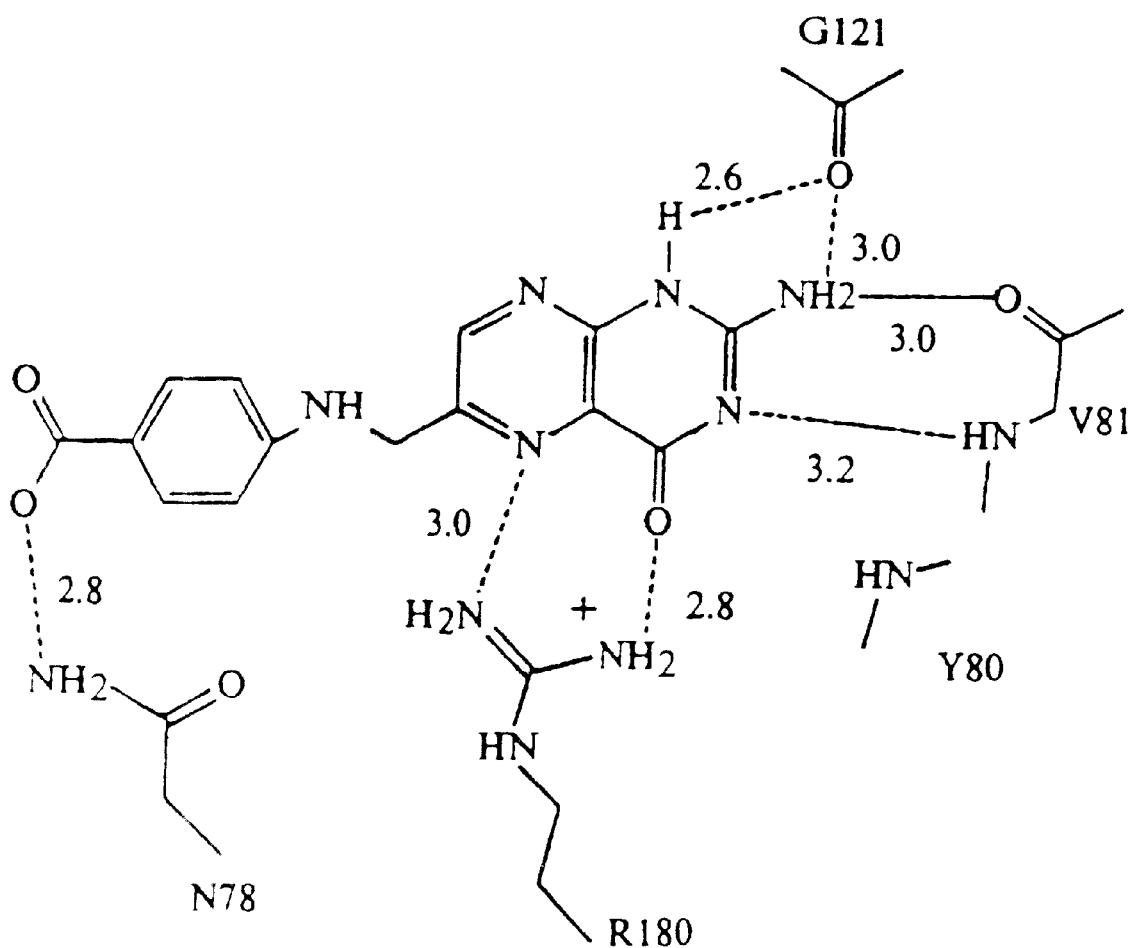
FIG. 5 illustrates the interactions between pteroic acid and RTA. Hydrogen bonds are shown as dashed lines with the lengths indicated.
Figure 6B:
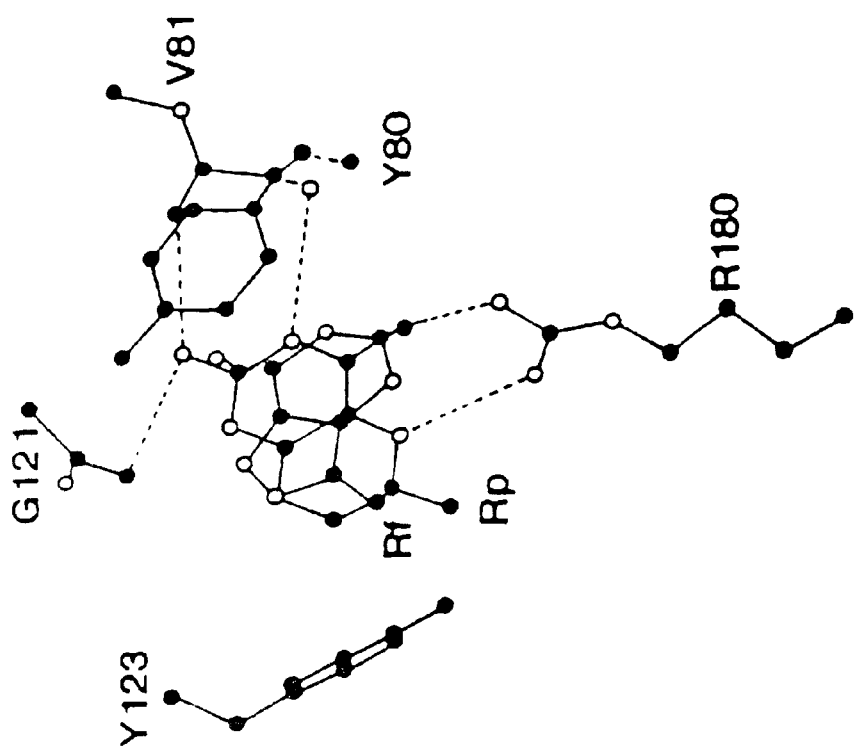
FIGS. 6A and 6B show the superposition of the formycin and pterin rings in the RTA active site. Carbon atoms are solid, nitrogen atoms have a light pattern and oxygens have a darker pattern. Hydrogen bonds between PTA and RTA are dashed lines and those between FMP and RTA (Monzingo and Robertus, *J. Mol. Biol.* 227:1136–45 (1992)) are dotted.
Figure 6A:
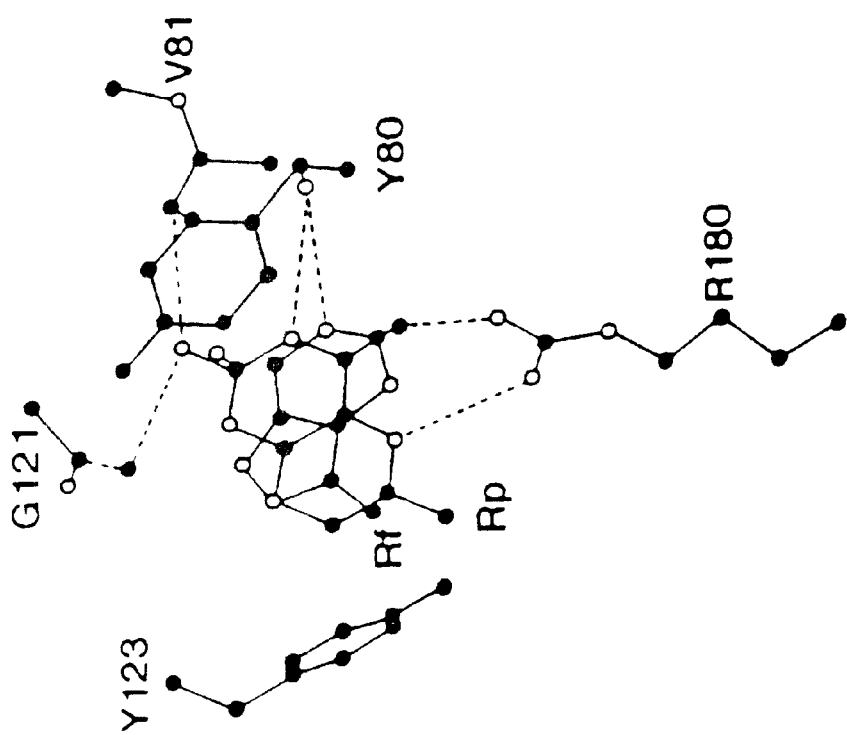

FIG. 5 illustrates the interactions between PTA and the active site of RTA. The pterin ring binds in roughly the position of the substrate adenine, sandwiched between the rings of Tyr 80 and Tyr 123. For comparison, FIGS. 6A and 6B show a superposition of the formycin ring of FMP (Monzingo and Robertus, *J. Mol. Biol.* 227:1136–45 (1992)) and the pterin ring of PTA. The 2.6 Å distance between N1 of pterin and the carbonyl oxygen of Gly 121 suggests that the pterin is stabilized in a tautomeric form with a hydrogen on N1 (shown in Table 2) and this can be donated to the carbonyl group. Note that the 2-amino group of pterin also donates a hydrogen bond to the carbonyl oxygens of Gly 121 as well as to Val 81; this roughly mimics the role of the 6-amino group on an adenine substrate. In the same way, N3 of pteroic acid resembles N1 of adenine, receiving a hydrogen bond from the amido N of Val 81. The adenine substrate receives a hydrogen bond at N3 from Arg 180, and indeed this is the likely route of substrate protonation in the catalytic mechanism. Pteroic acid receives two hydrogen bonds from Arg 180, at the 4-oxo and N5 positions.

The benzoate moiety of PTA bends around the side chain of Tyr 80 and probably makes some nonpolar interactions with it. In fact, the benzoate ring appears to bind on the surface of a pocket—a site hypothesized by Monzingo and Robertus, *J. Mol. Biol.* 227:1136–45 (1992), to be a second recognition site which may accommodate the guanine base of a natural rRNA substrate. Two hydrogen bonds are made to the benzoate, one between the carboxylate and Asn 78, and one to a water molecule which also bonds Arg 258. Although the pterin moiety of PTA makes strong and specific interaction within the adenine recognition site, it seems apparent that the benzoate moiety of PTA is not optimized for interactions within the second site.

EXAMPLE 5

Screening Additional Compounds

Following the analysis of PTA, structural and kinetic studies were carried out on a number of other pterin-based compounds, as shown in Table 2. These compounds differ essentially in the size of the group attached to pterin at position 6.

Table 2 will be inserted

Neopterin is pterin with propane triol at the six position. It was observed in the protein synthesis assay to be a modest inhibitor of RTA, with a Ki>2 mM (data not shown). Monoclinic crystals of an RTA complex were obtained by cocrystallization; they were isomorphous with the native, and diffracted to 2.5 Å resolution. 58,838 observations of 9,030 reflections to 2.5 Å resolution were collected ($R_{merge}$= 6.6%), the data reduced, and difference Fourier maps calculated. The pterin ring bound in the site previously seen to bind the formycin ring of FMP (Monzingo and Robertus, *J. Mol. Biol.* 227:1136–45 (1992) and the pterin ring of PTA as described above. As with PTA and FMP, the side chain of Tyr 80 was displaced by the ligand. Neopterin was positioned by hand, including the propane triol moiety, and X-PLOR used to adjust position of the ligand and the protein in a simulated annealing refinement; the R factor refined to 19.5% for all data. Coordinates for both the PTA and neopterin complexes have been submitted to the Brookhaven Protein Data Bank.

Figures 7A, 7B:
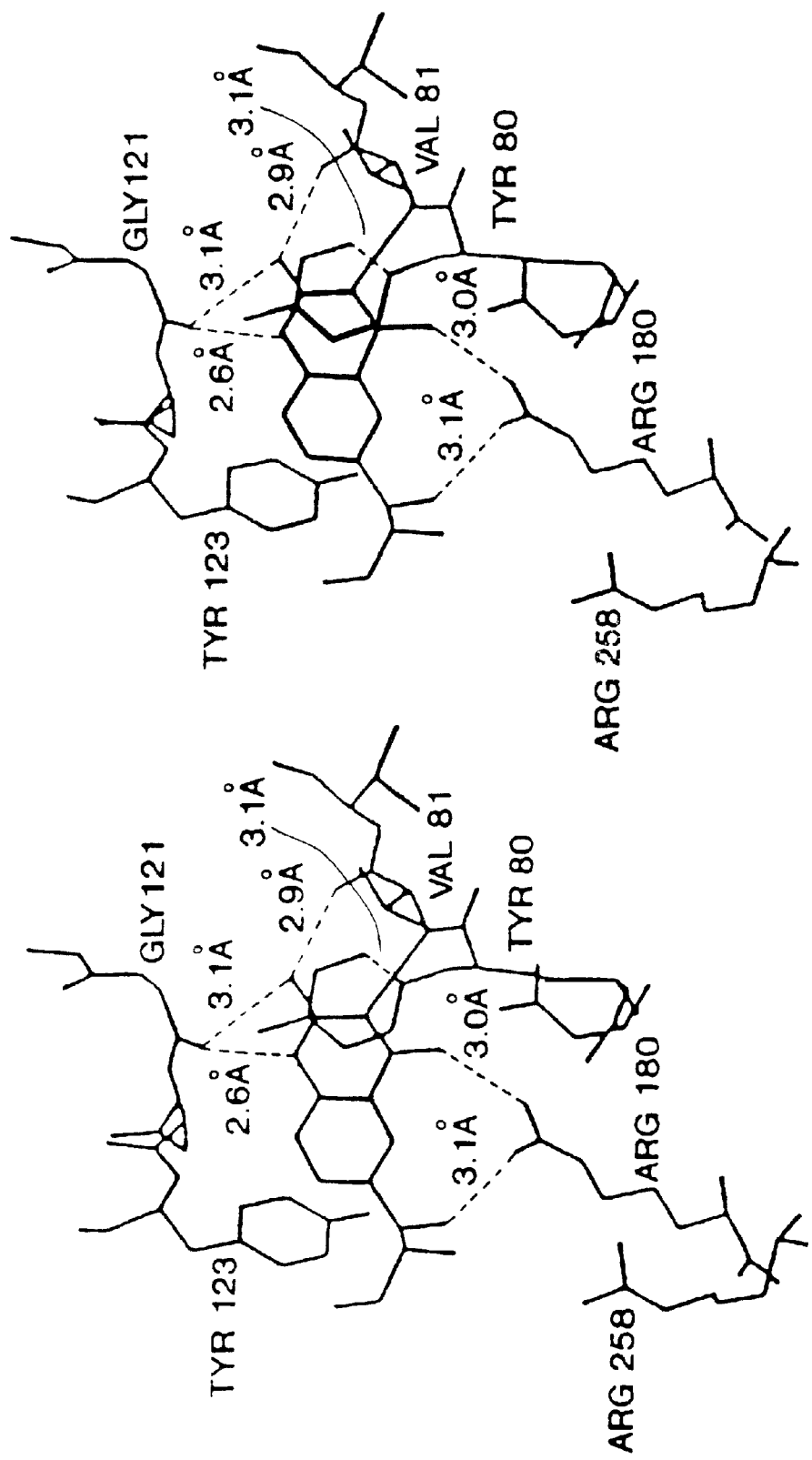
FIGS. 7A and 7B show the binding of neopterin in the RTA active site. Hydrogen bonds are shown as dashed lines and the lengths are indicated.
Figure 8A:
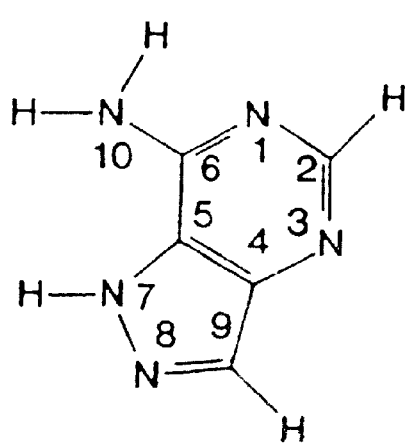
FIGS. 8A–8D show the structure and numbering of important substrate analogs for RTA. Nucteosides based on adenine, guanine, and formycin are linked to ribose at ring position 9. Pterin derivatives discussed in this specification are modified at position 6.
Figure 8B:
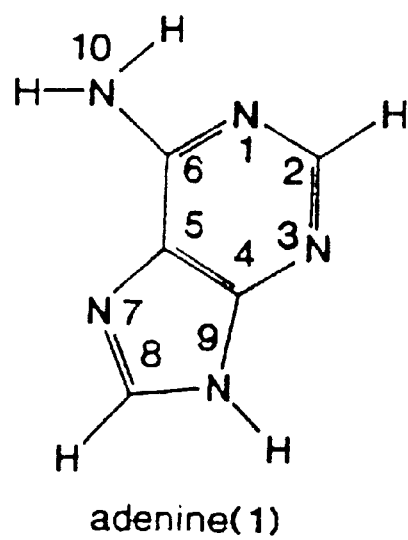
Figure 8C:
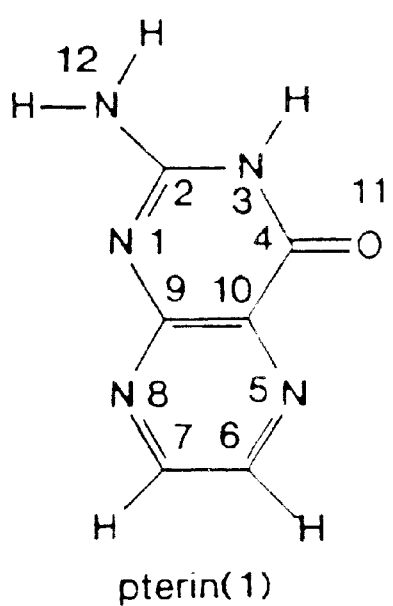
Figure 8D:
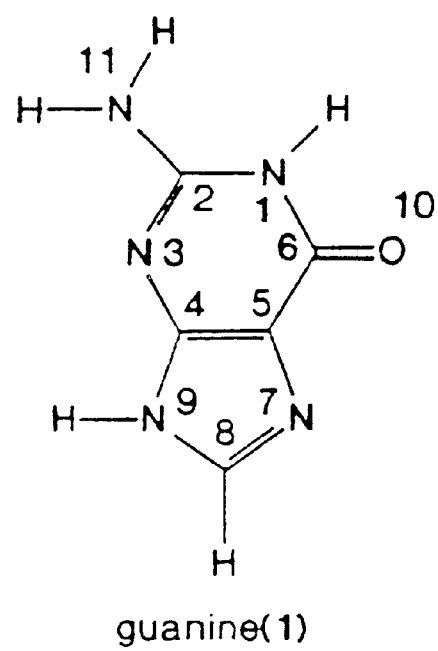

The binding of neopterin to RTA is shown in FIGS. 7A and 7B. The orientation of the pterin ring is similar to that seen for PTA. One difference is the bonding of Arg 180 to the inhibitor. It bonds to the 4-oxo group of neopterin, but does not bond to N5 as occurs in the PTA complex. Instead, a second bond is formed with the proximal hydroxyl of the propane triol moiety. Associated with this rearrangement is a 7° rotation of the pterin ring. The other atoms of the propane triol moiety of neopterin make no interaction with RTA. Since the propane triol moiety of neopterin is much smaller than the corresponding substituents in PTA, it does not interact with Tyr 80 in, the same way and appears to lack the van der Waals contribution to binding which might be expected in PTA. This is consistent with energy calculations using SYBYL, which show interruption enthalpies between RTA and PTA to be −106 Kcal/mole and those between RTA and neopterin to be −73 Kcal/mole. Kinetic inhibition data, although not definitive, also suggest PTA is a better inhibitor and more likely to exhibit tighter binding. The stronger binding of PTA compared with neopterin argues that design of a pterin-based moiety derivatized at the 6 position which makes a strong and specific interaction with RTA is the preferred approach in creating an efficient inhibitor.

Crystals of RTA•neopterin were isomorphous with native RTA, but crystals of RTA•PTA were reproducibly not isomorphous; RTA•PTA crystals exhibited a contraction of about 3 Å along both the a and c axes. A least squares superpositioning of the two complexes showed very few significant structural differences between them. The largest changes were at the N and C termini, both far removed from the substrate (inhibitor) binding site. The chemical differences between the two inhibitors are centered on the size and charge of the moiety derivatizing pterin at position 6. However, there are no direct interactions of the bound inhibitor with any crystallographically-related molecules. Furthermore, the protein conformation itself is very similar in these two active sites, and so it does not appear that inhibitor binding induces protein changes which then are involved directly in crystal packing. It may be that inhibitor binding triggers a series of very subtle changes which propagate throughout the protein and cause a rearrangement of packing, although this seems unlikely. It is also possible that saturating the solution with PTA has an unspecified solvent effect which tends to dehydrate the crystals and causes them to shrink. Except for this phenomenon, the binding of the two inhibitors seems to have roughly the same effect on RTA conformation, moving the Tyr 80side chain. Further, inhibitor design can use this observed binding as a foundation and that novel inhibitor models can be fit to this template without undo concern about predicting protein responses.

Neither pterin-6-carboxylic acid nor folic acid acted as inhibitors of RTA within the limits of their solubility. Efforts to soak the compounds into monoclinic crystals, even at saturating conditions, and cocrystallization efforts failed to produce stable complexes for X-ray analysis.

Given knowledge of the binding of PTA and neopterin it was predictable that neither pterin-6-carboxylic acid nor folic acid would bind to RTA. Refinement and energy minimization using SYBYL suggested that the interaction enthalpy for pterin-6-carboxylic acid, with one negative charge, was low (−64 Kcal/mole) -compared with PTA or neopterin. Inspection of the hypothetical binding, assuming that the pterin moiety assumes the position seen in PTA, suggests that the 6 carboxylate is near the Glu 177 residue of RTA. Charge repulsion may therefore prevent binding of this simple compound.

Folic acid does not inhibit RTA, nor does it bind to RTA crystals. Folic acid resembles PTA accept that the benzoic acid moiety is derivatized with long and negatively charged glutamic acid. Electrostatic mapping of the RTA surface shows the mouth of the second recognition site, beyond the area binding the PTA benzoate, is generally negative due to the presence of residues like aspartates 75, 96, and 100. This negative charge likely repels the folic acid group, driving it into solution and limiting binding compared with PTA.

Figure 10G:
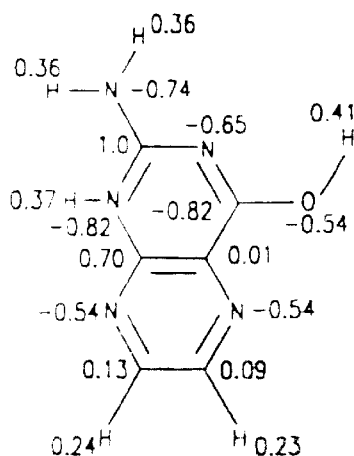
FIGS. 10A–10T show the chemical structures and partial charges for ring compounds examined in this study. Charges were derived from ab initio minimization and used in subsequent docking experiments with RTA.
Figure 10H:
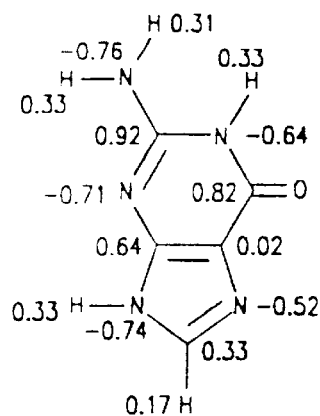
Figure 10I:
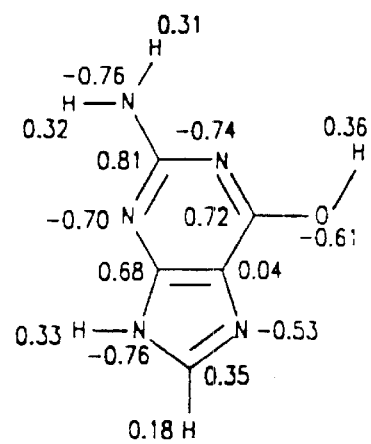
Figure 10J:
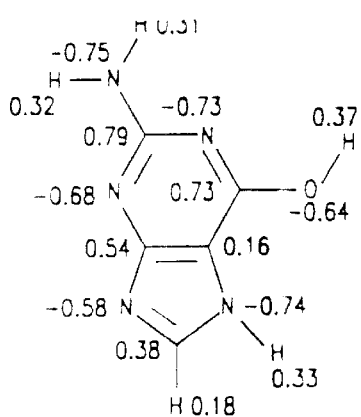
Figure 10K:
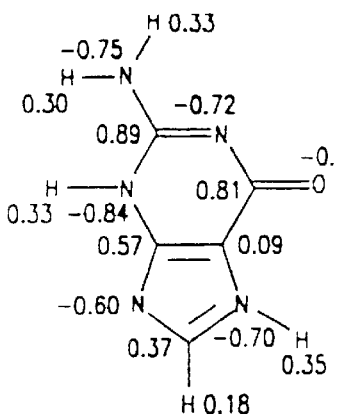
Figure 10L:
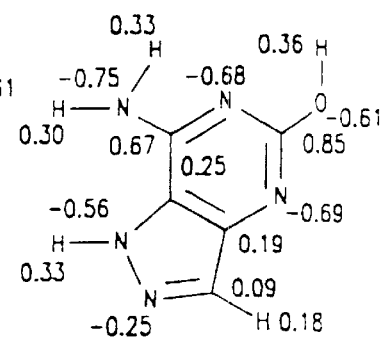
Figure 10M:
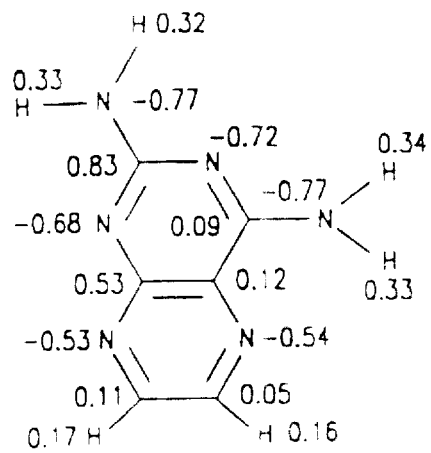
Figure 10N:
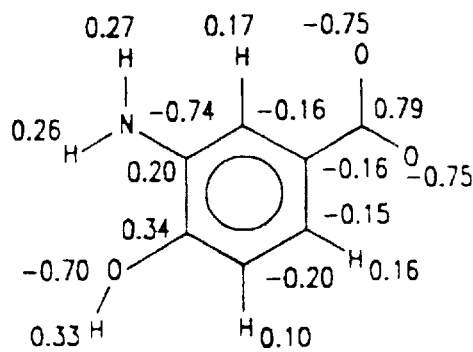
Figure 10O:
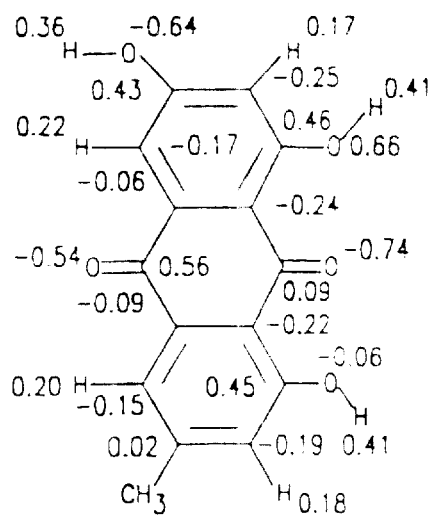
Figure 10P:
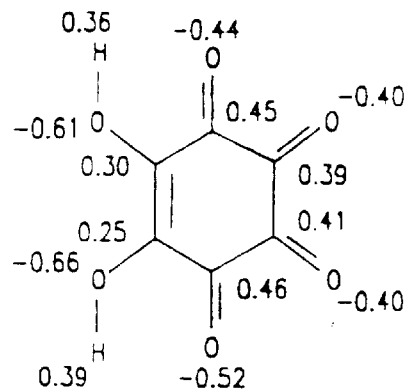
Figure 10Q:
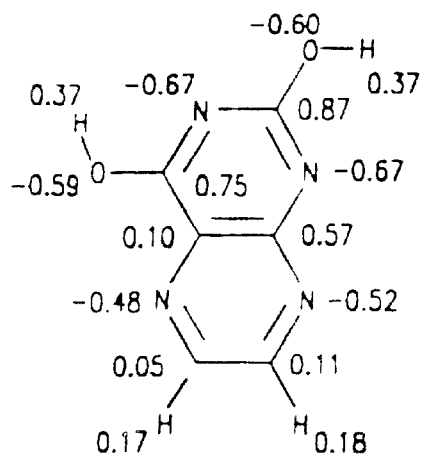
Figure 10R:
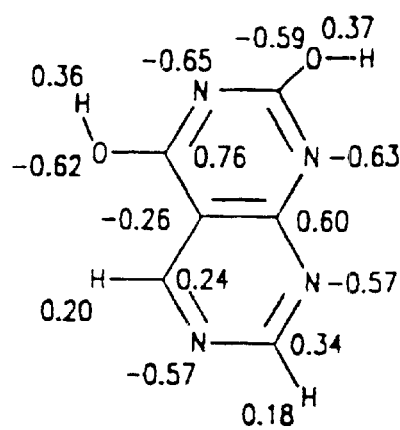
Figure 10S:
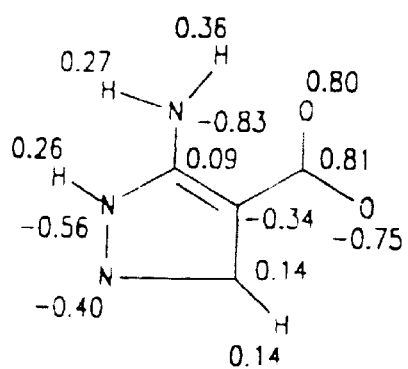
Figure 10T:
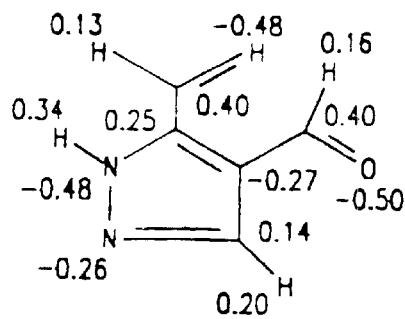

FIGS. 10A–10T show the net atomic charges, derived from ab initio minimization with the 6–31 g** basis set, on additional ligands examined by the methods of the present invention. Table 3 lists the molecular energies of these compounds in atomic units, au, where 1 au=627.5 Kcal. Table 3 also lists the interaction energies between RTA and each ligand calculated from molecular mechanics methods (Tripos force field). The interaction energies are broken into Van der Waals and electrostatic components. The active site binding geometries for the energy minimized complexes with formycin, adenine, pterin(1), pterin(3) and guanine(4), computed by molecular mechanics, are presented in FIGS. 11A–11F.

TABLE 3 molecular energy (au) from ab initio minimization and interaction energy (Kcal/mol) between ricin and these structures from molecular mechanics minimization

Figure 9A:
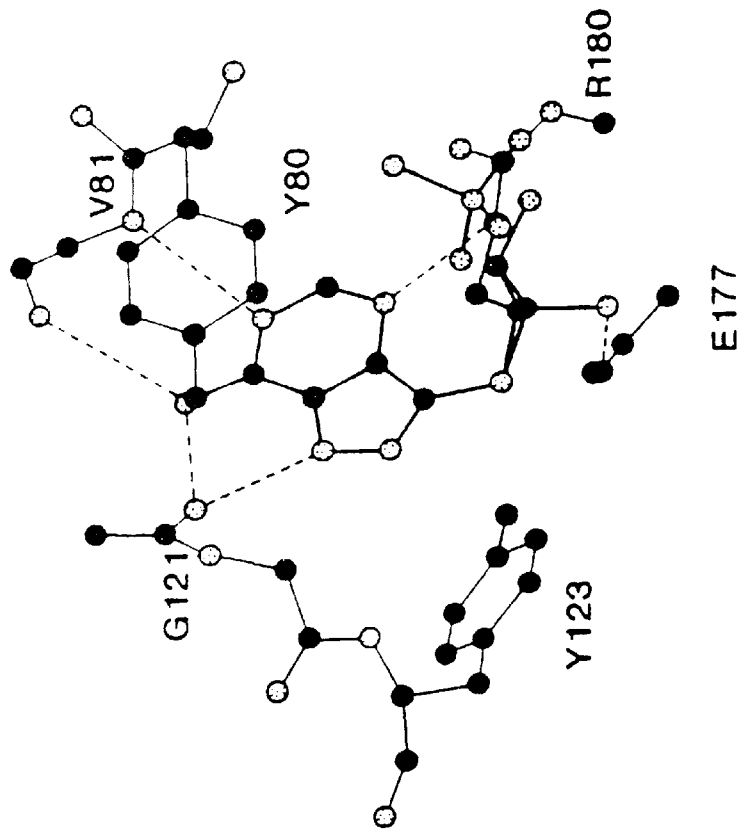
FIGS. 9A and 9B show the crystallographically observed complex of RTA and FMP. The figure shows the substrate recognition cleft occupied by FMP, an AMP analog. Hydrogen bonds are shown as dashed lines, bonds within RTA are lighter than those within FMP. Carbon and hydrogen atoms are black, oxygen is a light pattern, and nitrogen and phosphorous are a darker pattern.
Figure 9B:
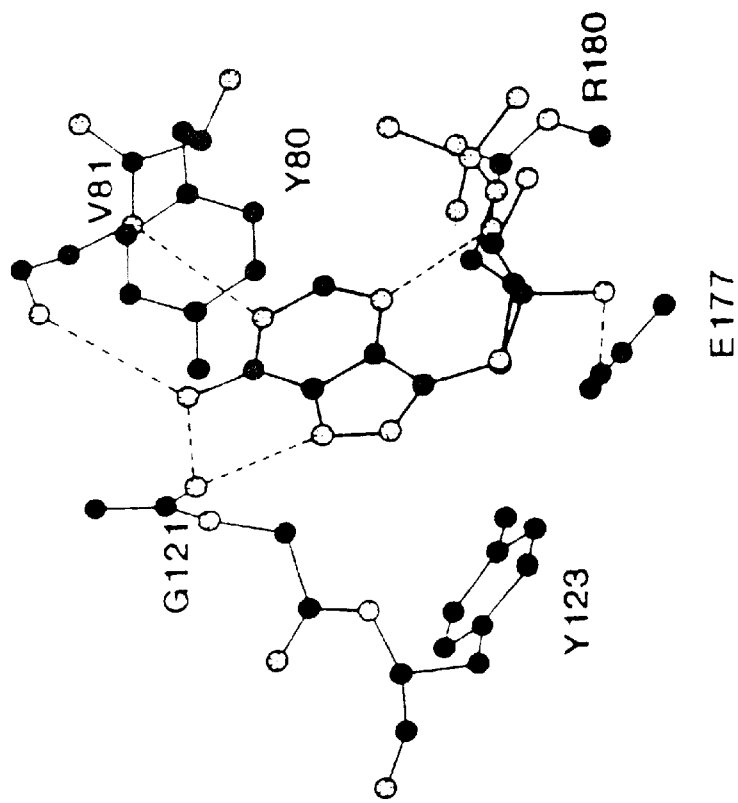
Figure 11A:
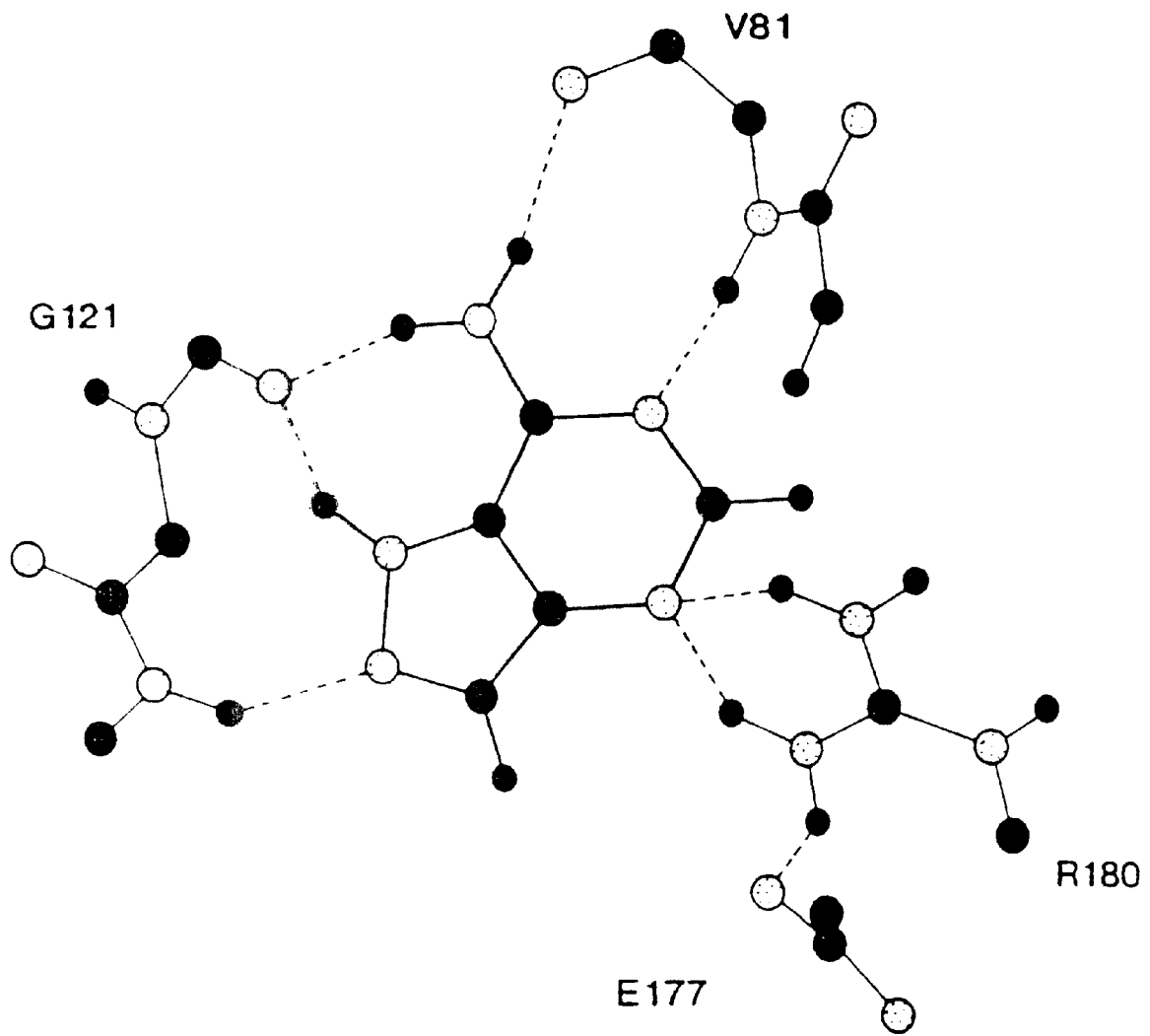
FIGS. 11A–11F show the bonding interactions predicted between RTA and various ring compounds. Partially charged compounds were docked into RTA and minimized in SYBYL. Hydrogen bonds are shown as dashed lines, bonds within RTA are lighter than those within the ligand; carbon and hydrogen atoms are black, oxygen is a light pattern, and nitrogen is a darker pattern. The Figure shows RTA interactions with a) formycin ring, b) adenine, c) pterin(1) tautomer, d) pterin (3) tautomer, e) guanine(4) tautomer, and f) AHA (3-amino-4-hydroxybenzoic acid).

| molecular structure | energy (au) | Interaction energy (Kcal/mol) | | |
|---|---|---|---|---|
| | | vdw | electrostatic | total |
| formycin | −464.4888712 | −19.2 | −24.5 | −43.7 |
| adenine(1) | −464.5361520 | −18.0 | −19.4 | −37.4 |
| adenine(2) | −464.5211196 | −19.0 | −20.5 | −39.5 |
| Pterin(1) | −577.2721321 | −23.1 | −22.0 | −45.1 |
| pterin(2) | −577.2702506 | −22.8 | −21.8 | −44.6 |
| pterin(3) | −577.2624667 | −22.6 | −31.8 | −53.4 |
| pterin(4, ion) | −577.6574933 | −22.9 | −24.6 | −47.5 |
| guanine(1) | −539.4125625 | −18.7 | −16.1 | −34.8 |
| guanine(2) | −539.4129359 | | | |
| guanine(3) | −539.4055644 | −21.8 | −20.0 | −40.8 |
| guanine(4) | −539.4005964 | −20.8 | −33.0 | −53.8 |
| 2-hydroxy formycin | −539.3674887 | −18.7 | −29.1 | −47.8 |
| 2,4-diamino-pteridine | −557.4495408 | −23.2 | −18.9 | −42.1 |
| aha(ion) | −547.6530542 | −19.6 | −48.5 | −68.1 |
| emodin | −948.2356142 | −30.0 | −44.0 | −74.3 |
| rhodizonic acid | −677.4887203 | −19.6 | −25.5 | −45.1 |
| lumazine | −597.0937652 | −17.5 | −22.5 | −40.0 |
| S1 | −597.1110054 | −18.0 | −25.7 | −43.7 |
| S2(ion) | −466.8918064 | −14.5 | −41.1 | −55.6 |
| S3 | −450.2572027 | −15.7 | −24.1 | −39.8 | vdw - van der Waals interaction energy (kcal/mol);
aha - 3-Amino-4-hydroxybenzoic acid Based on energy minimization, the formycin ring structure forms 7 hydrogen bonds in the RTA binding site (FIG. 11A). The ligand has an interaction energy with RTA of −43.7 Kcal/mol. The calculated orientation of the free formycin generally is similar to the ring seen crystallographically in the RTA•FMP complex (FIGS. 9A and 9B). However, note the free ring is shifted slightly so that an extra hydrogen bond is donated by the backbone NH of Tyr 123 to N8 of formycin. In addition, the guanidinium of Arg 180 donates two bonds instead of one to N3. The lack of the ribose ring allows the Arg 180 side chain to reorient in this way.

Figure 11B:
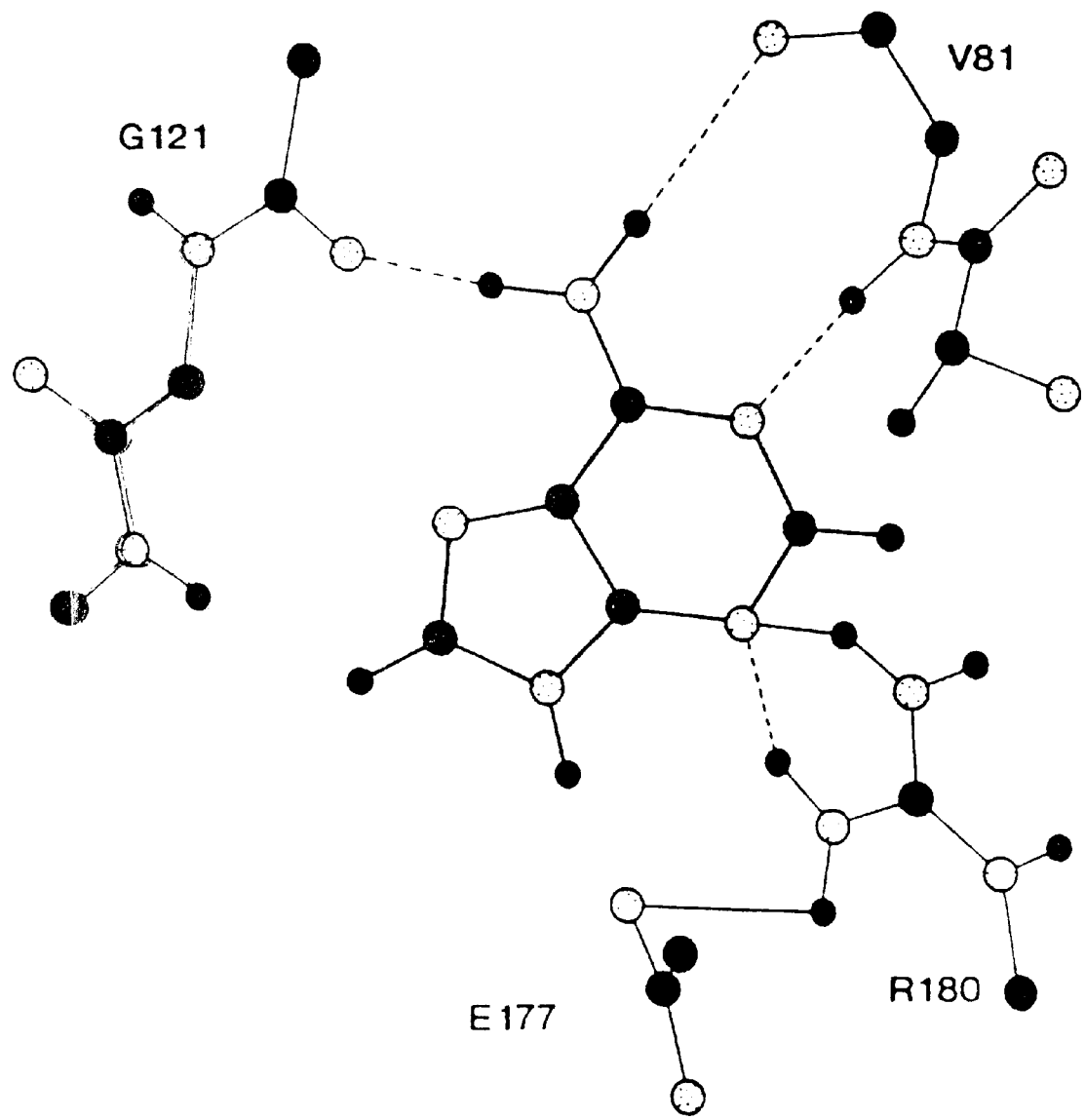
Figure 11C:
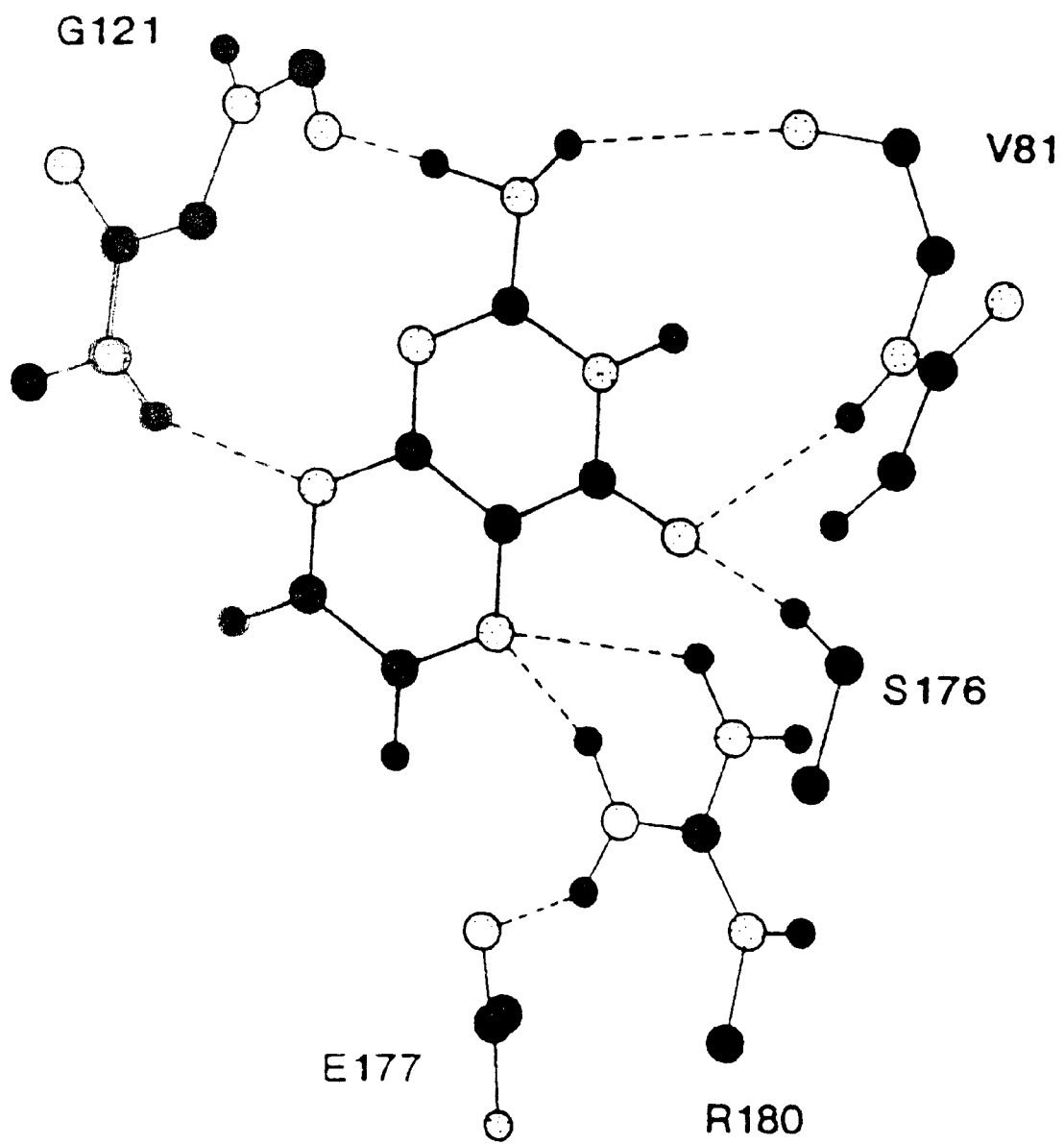
Figure 11D:
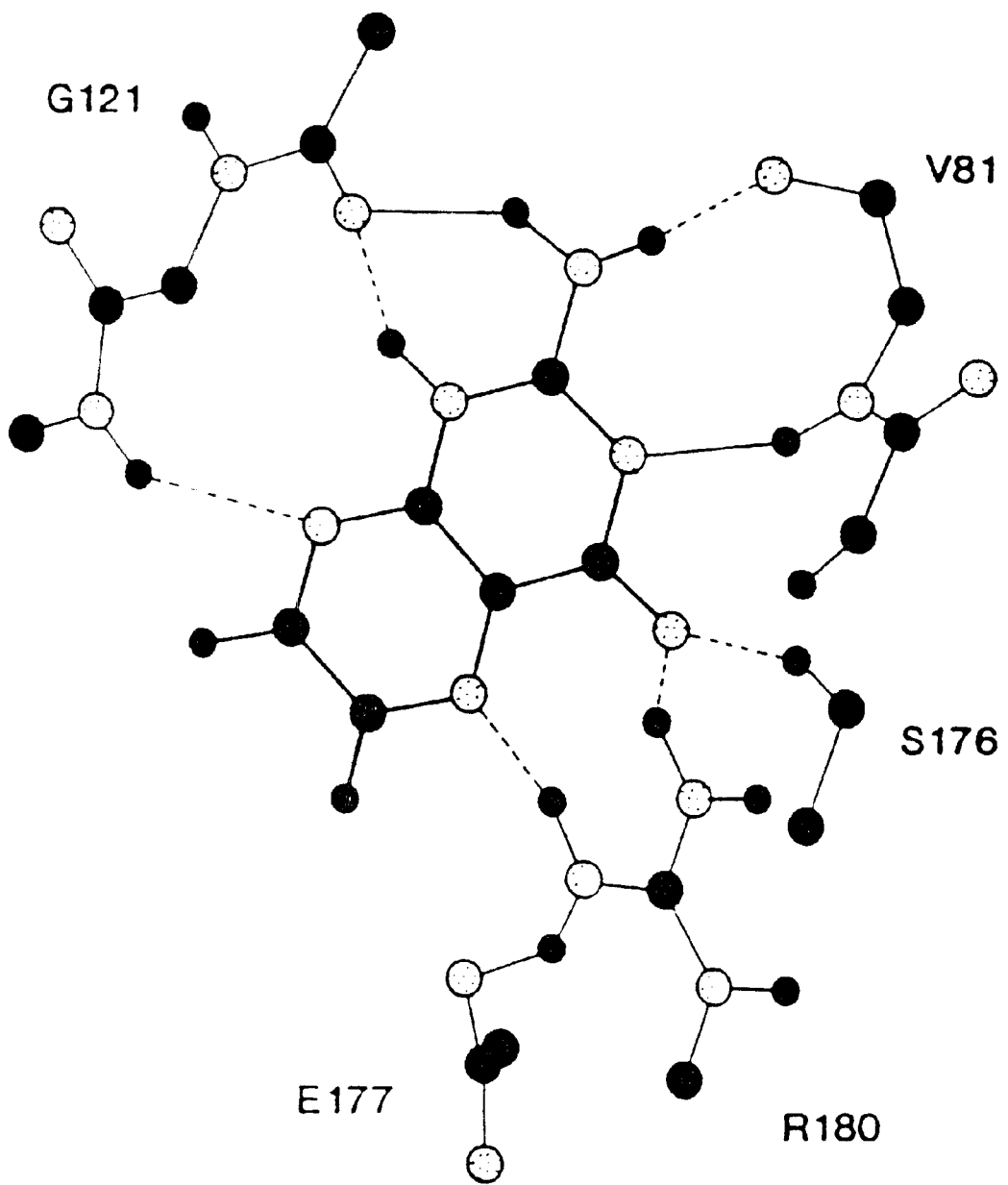

Adenine is the natural substrate for RTA and is recognized by the enzyme, at least when it is part of a GAGA loop context. For the two major adenine tautomers (see FIGS. 10A–10T), the molecular energy of adenine(1) is 9.4 Kcal/mol (0.015 au) lower than adenine(2), suggesting it is the normal solution form. Adenosine nucleotides are derivatized at N9 and so are frozen into the tautomer(1) form. FIG. 11B shows the interaction of adenine(1) with RTA. Table 3 shows that the free adenine(2) interacts slightly more strongly with RTA than does adenine(1). The main reason for this is that in adenine(2) the hydrogen on N7 can be donated to O of Gly, 121. Weston et al., *J. Mol. Biol.* 244:410–422 (1994), found that AMP was hydrolyzed in a tetragonal form of RTA crystals leaving only adenine bound. The occupancy was low, however, and it was not possible to assess the tautomeric form of adenine. In the design of inhibitors, derivatives of either form would seem equivalent.

Figure 1B:
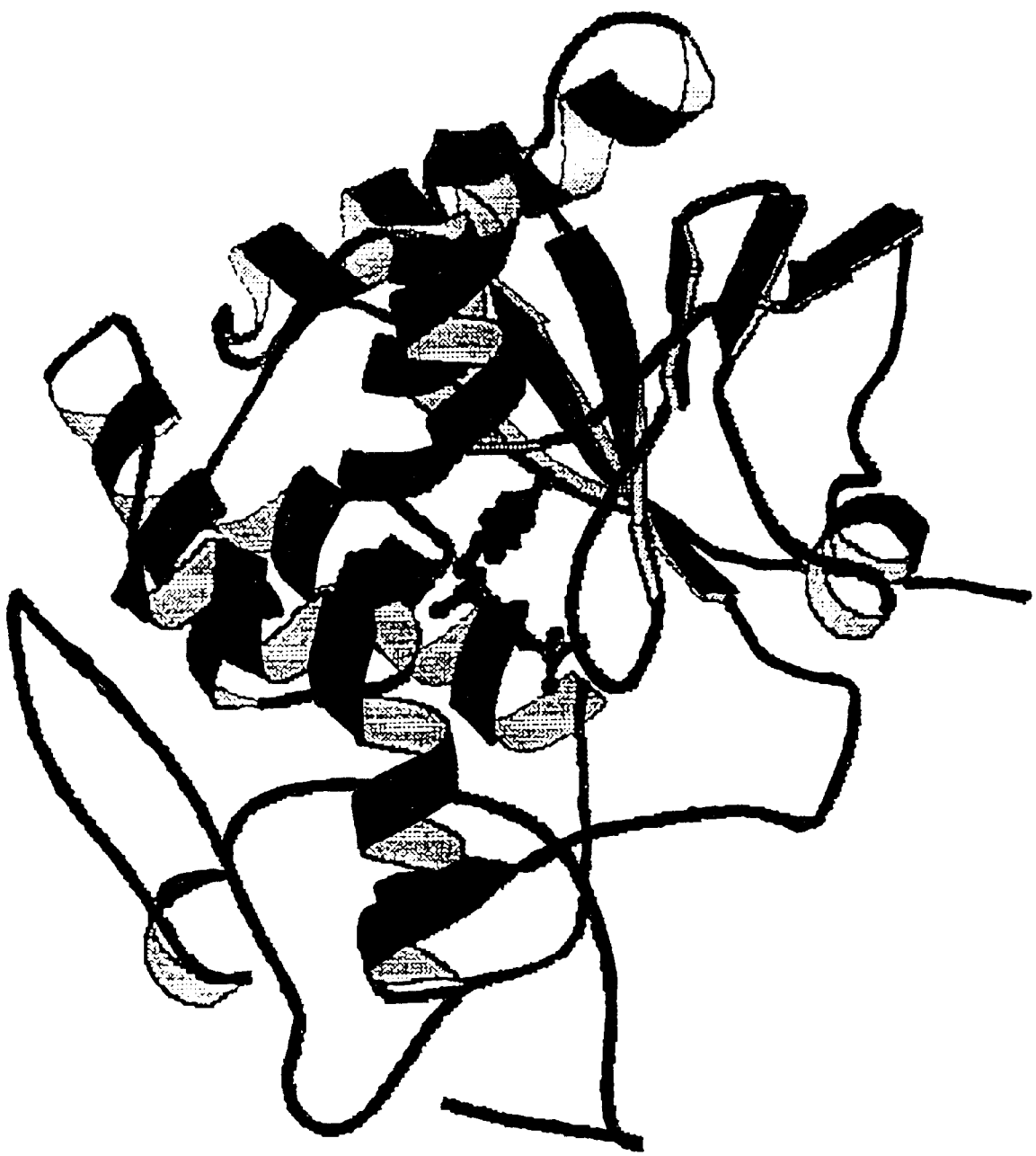
Figure 2:
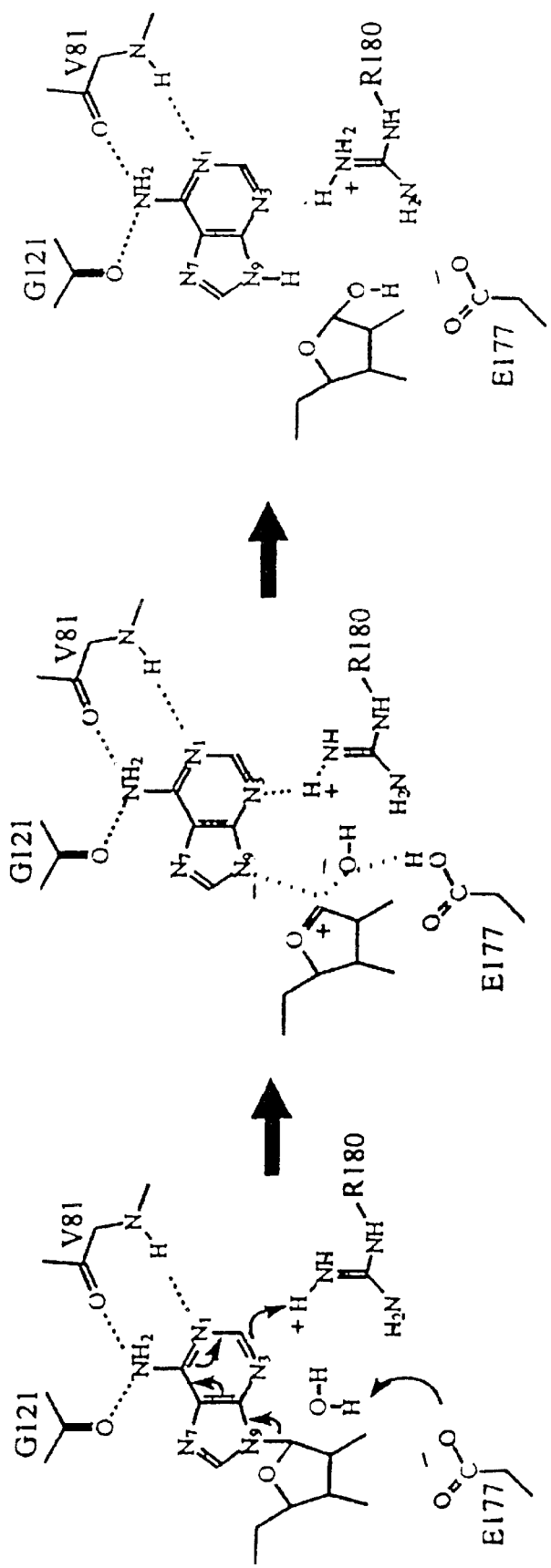
FIG. 2 shows the reaction mechanism by which ricin depurinates an adenine residue in 28 S rRNA.

The interaction energies between RTA and the four underivatized pterin tautomers (one is in the ion form) were minimized and are listed in Table 3. Pterin(1), the most stable tautomer in aqueous solution, has an interaction energy around −45 Kcal/mol (FIG. 11C), as strong as for formycin. The exocyclic 6-amino (N12 in FIG. 1), donates hydrogen bonds to O of Gly 121 and Val 81, reminiscent of the amine group in formycin and adenine. The 4-oxo atom (O11 in FIGS. 8A–8D) receives bonds from NH of Val 81 and the Oγ of Ser 176, while N8 receives a bond from the NH of Tyr 123 and N5 receives two bonds from Arg 180. Because the interaction energy is as strong as for formycin, it is reasonable to assume that pterin(1) may bind weakly in the RTA active site. However, pterin(1) forms fewer and generally weaker hydrogen bonds with RTA than does pterin(3), shown in FIG. 11D. A comparison of the binding of the two pterin forms is also diagrammed in FIGS. 12A and 12B, where strong hydrogen bonds are shown as dashed lines and weaker ones as dotted lines. It shows the pterin(1) complex forms three strong and four weak bonds, while pterin(3) complex forms six strong and two weak bonds. In particular, loss of the hydrogen from N3 of pterin(1) allows that atom to receive a bond from the NH of Val 81 (2.8 C), and acquisition of a hydrogen at N1 allows it to donate a bond to the O of Gly 121 (2.6 C). Consistent with this, the interaction energy for pterin(3) is about 8 Kcal/mole more favorable than for pterin( 1). The X-ray data are consistent with the binding of pterin(3). The observed distance between pterin N3 and the backbone N of Val 81 is 3.2 C, impossible if both have hydrogens on them. Also the distance between O of Gly 121 and N1 and the exocyclic N of pterin are 2.6 and 2.8 Å respectively, suggesting two strong hydrogen bonds. It is apparent that the increased stability of binding tautomer (3) to RTA compensates for the cost of shifting from the more stable tautomer(1).

It is apparent from the interaction energies that the strong binding of PTA results not only from interactions with the pterin ring, even its tautomer(3) form, but also from additional interactions with the benzoate-containing group linked at C6. Compared with PTA, the free pterin group also orients in a slightly different fashion based on molecular mechanics calculations. In particular, a hydrogen bond can be formed from Oγ of Ser 176 to the 4-oxo of free pterin, whereas this is much weaker (3.4 Å) in the PTA complex. However, Ser 176 should be exploited in the design of inhibitors.

Figure 12B:
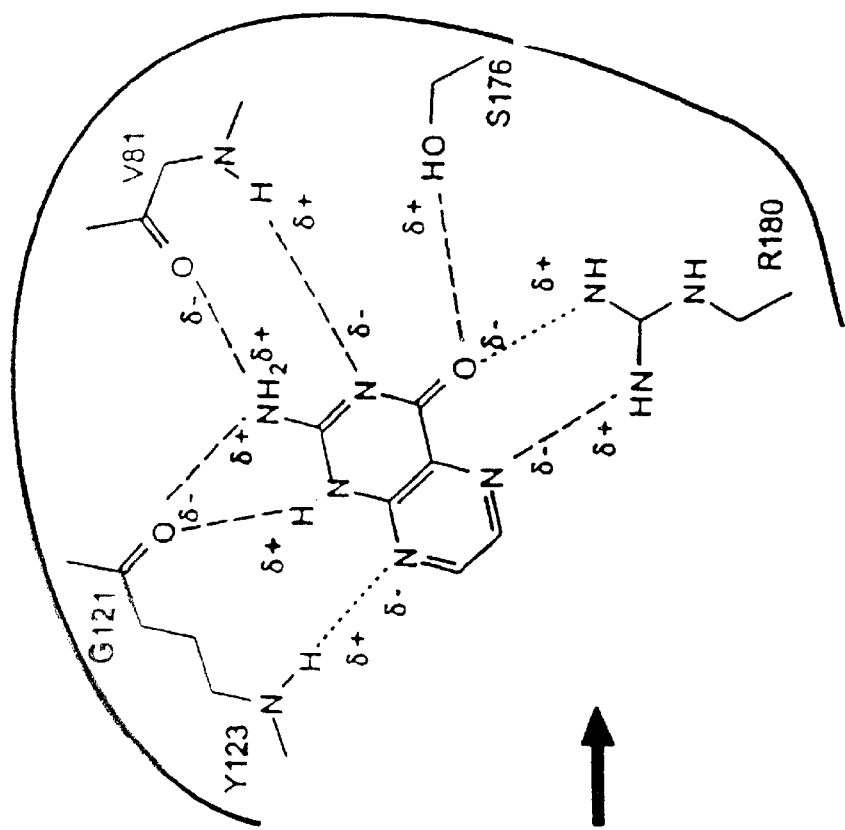
FIGS. 12A and 12B show the interactions between RTA and two forms of pterin. Panel A shows the hydrogen bonds and charge distribution of RTA interacting with pterin(1) and B shows the interactions with pterin(3). Strong bonds (2.6 to 2.8 Å) are dashed lines and weaker bonds (3.0 to 3.3 Å) are dotted. Partial charges are indicated by the δ symbol.
Figure 12A:
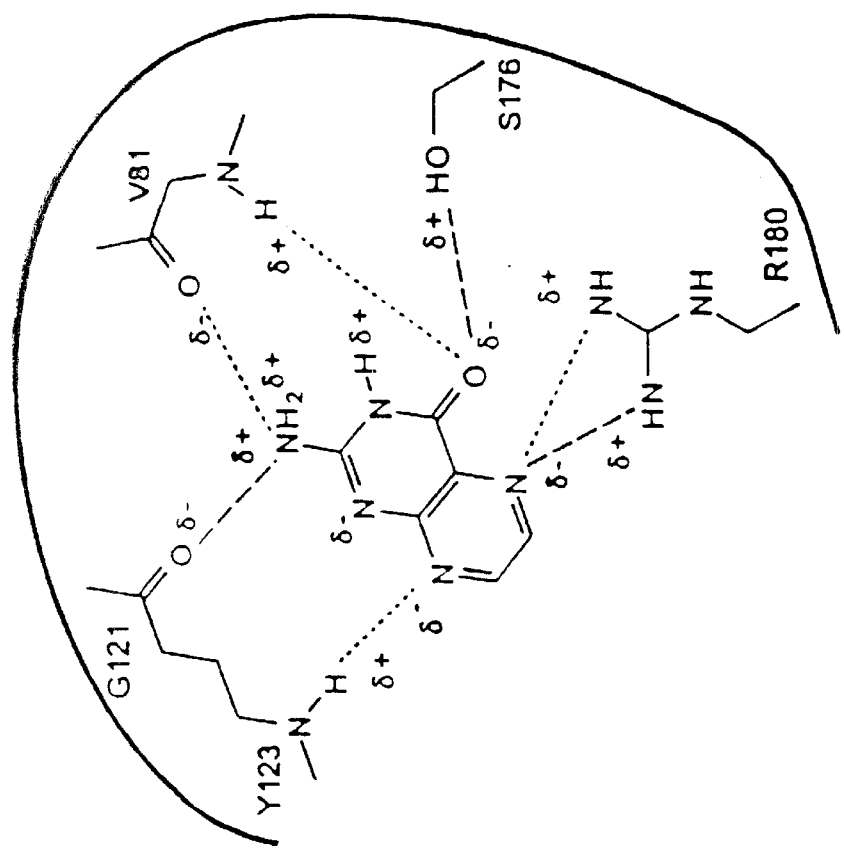
Figure 13B:
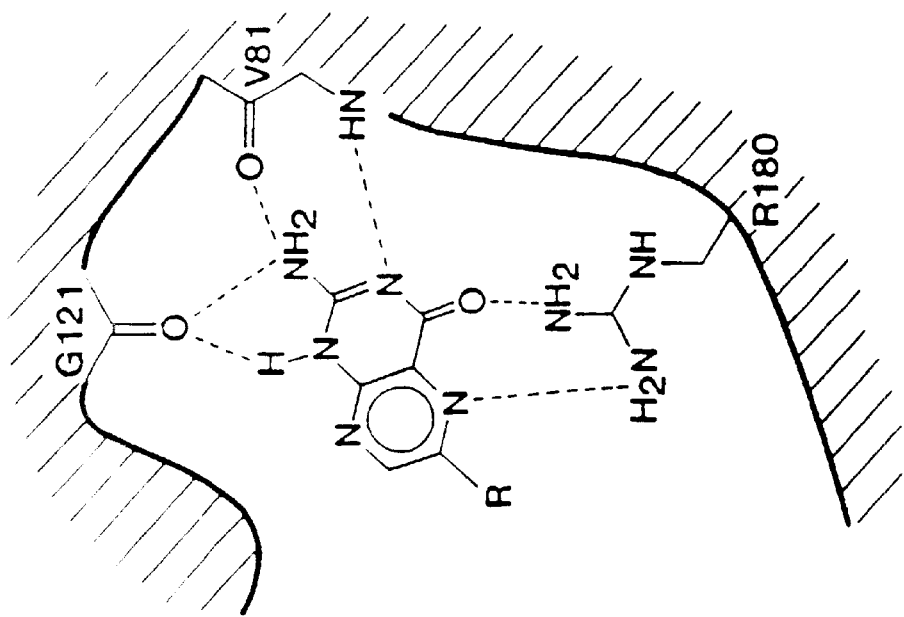
FIGS. 13A–13D show the correlation of ligand structure for the design of RTA inhibitors. Panel A shows the observed binding of nucleotides like FMP and AMP. Panel B shows the limitations of guanine nucleotides as ligands. Panels C and D show two representations for the binding of pterin based inhibitors. Panels C and D differ in the hydrogen binding of pterin to Arg 180.
Figure 13A:
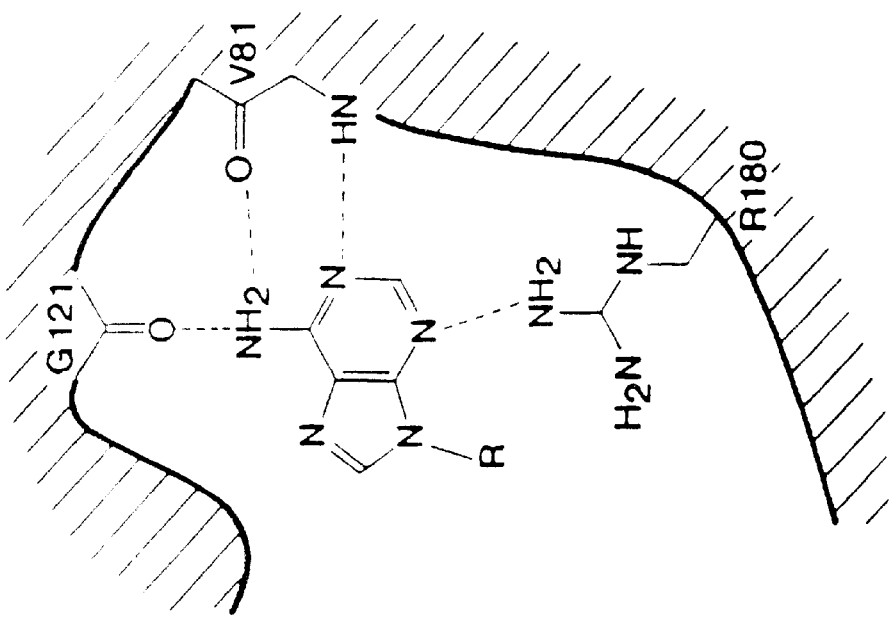
Figure 13D:
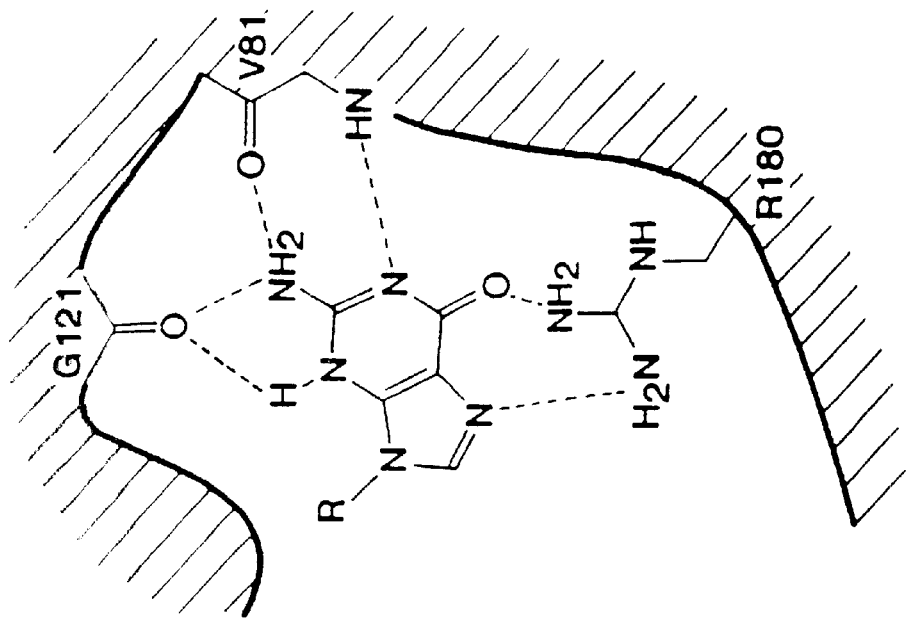
Figure 13C:
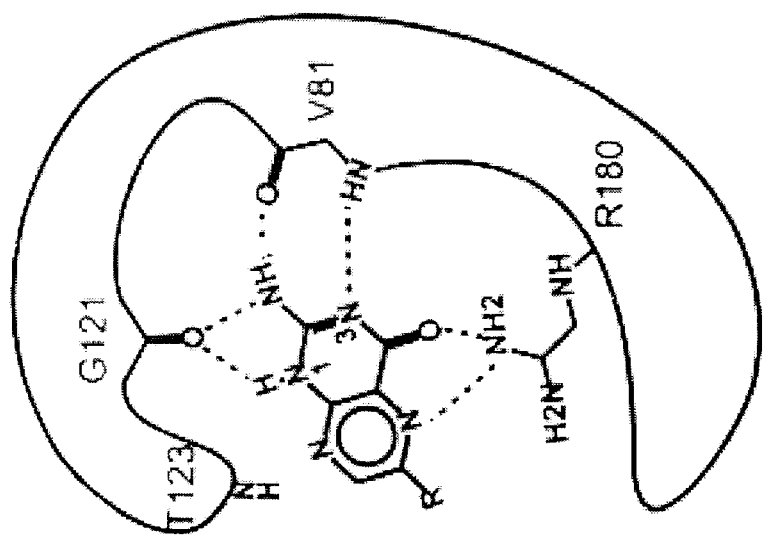

The binding of pterin(3) to RTA may result from simple equilibrium considerations. Pterin(3) is much less common in solution than form 1, but once bound the equilibrium shifts to produce more form 3. Alternatively, it may that the more stable pterin(1) initially recognizes the RTA active site. Then, a shift of the protons from N3 to N12 and a shift from N12 to N1 take place, creating the pterin(3) tautomer; FIGS. 12A and 12B illustrate this process. Tautomehization may be triggered by the repulsive forces between the positive charges on Arg 180, Ser 176, and Val 81 of the protein, and the positive charge on N3 of pterin(1). At the same time, there is an electrostatic attraction to move protons to N12 which is surrounded by negative charges from Gly 121 and Val 81.

Figure 11E:
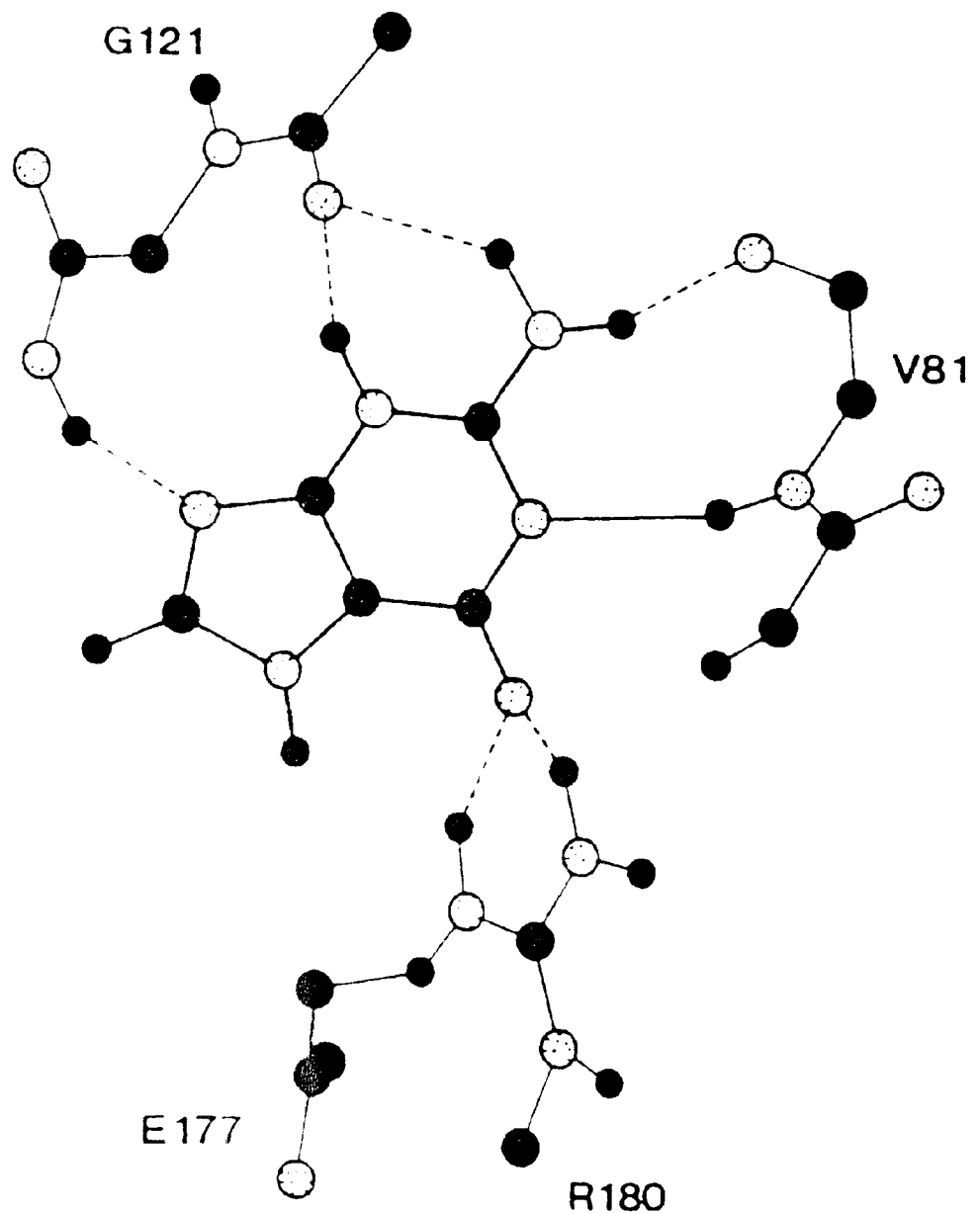

The success of binding pterins to RTA raises questions about binding guanine derivatives, which have many of the same chemical features as pterins. Ab initio calculation shows that guanine(1), the form seen in nucleotides, is a low energy tautomer, while guanine(4) is the highest. From the interaction energies in Table 3, it can be seen that the guanine(4) interacts most strongly with RTA, as strongly as pterin(3). This putative binding to RTA is shown in FIG. 11e, where the carbonyl (6-oxo) of guanine(4) accepts two hydrogen bonds from the guanidinium group of Arg 180, while other groups interact with RTA in a fashion similar to pterin(3). The stability of guanine(4) compared to guanine (1) arises from the same considerations as were described for pterin(3) binding compared to pterin(1). Interaction energy calculations suggest guanines are reasonable inhibitor candidates. Attempts to bind 2-amino-6,8-dihydroxypurine (8-hydroxy guanine) to RTA were unsuccessful although the solubility of such compounds is limited and crystallization conditions may not allow strong binding to occur.

Since the interaction energies of guanine compounds is computed to be high compared to adenine, one might ask about the specificity of RTA for adenine. FIGS. 13A–13D integrate information about the bonding of adenines, pterins, and guanines. It shows that guanine nucleotides cannot bind to the RTA active site for trivial steric reasons. Panel A shows the binding of adenine-like nucleotides such as FMP and ApG seen crystallographically. The R group would be a ribose linking the base into a larger rRNA molecule. Panel B and C show alternative binding schemes for the binding of pterin based ligands (Panels B and C differ in the hydrogen binding between the pterin ligand and Arg180); PTA and neopterin are derivatized at position 6, shown by the R. Panel D shows that the guanine(4) base can assume an electronic configuration like pterin, but compared with adenine, it is flipped over. Note that the R group at position 7 now clashes with the protein. Non-nucleoside guanine compounds might still be expected to bind well to RTA if they are modified at positions 8 or 9. Compounds like 2-amino-6,8-dihydrooxypurine did not bind to RTA, but are poorly soluble and it simply may be that under crystal conditions these compounds cannot achieve high enough concentrations to bind well to the protein. On the other hand, it should be noted that, unlike pterin(1), the interaction energy of guanine(1) with RTA is quite low, about −34.8 Kcal/mol, compared to −45.1 Kcal/mol. If a model as shown in FIGS. 12A and 12B is appropriate, the initial recognition of guanine may be very unlikely.

In addition to the purine and pterin bases, a number of other compounds were analyzed as potential RTA inhibitors. The interaction energy of 2,4-diamino-pteridine with RTA is −42.1 Kcal/mol (Table 3). This energy is substantially weaker than for pterin because the 4-amino hydrogens repulse the guanidinium group of Arg 180 and N1 repulses the carbonyl O of Gly 121. Rhodizonic acid has 4 carbonyl groups and 2 hydroxyl groups; it might seem to be flexible enough to form a variety of interactions with RTA. Its interaction energy is about −45 Kcal/mole, similar to formycin, and yet it failed to bind to RTA crystals. It should be noted however, that the interaction energy for FMP is −89 Kcal/mole and the additional interactions outside the specificity pocket may b e important to judging the effectiveness of binding. In a similar fashion, lumazine, S1, and S3 (Table 3 and FIGS. 10A–10T) interact with RTA at only modest strength, implying that they are unlikely to b e good inhibitors of RTA themselves, but can serve as the parent compound for other inhibitor classes.

Figure 11F:
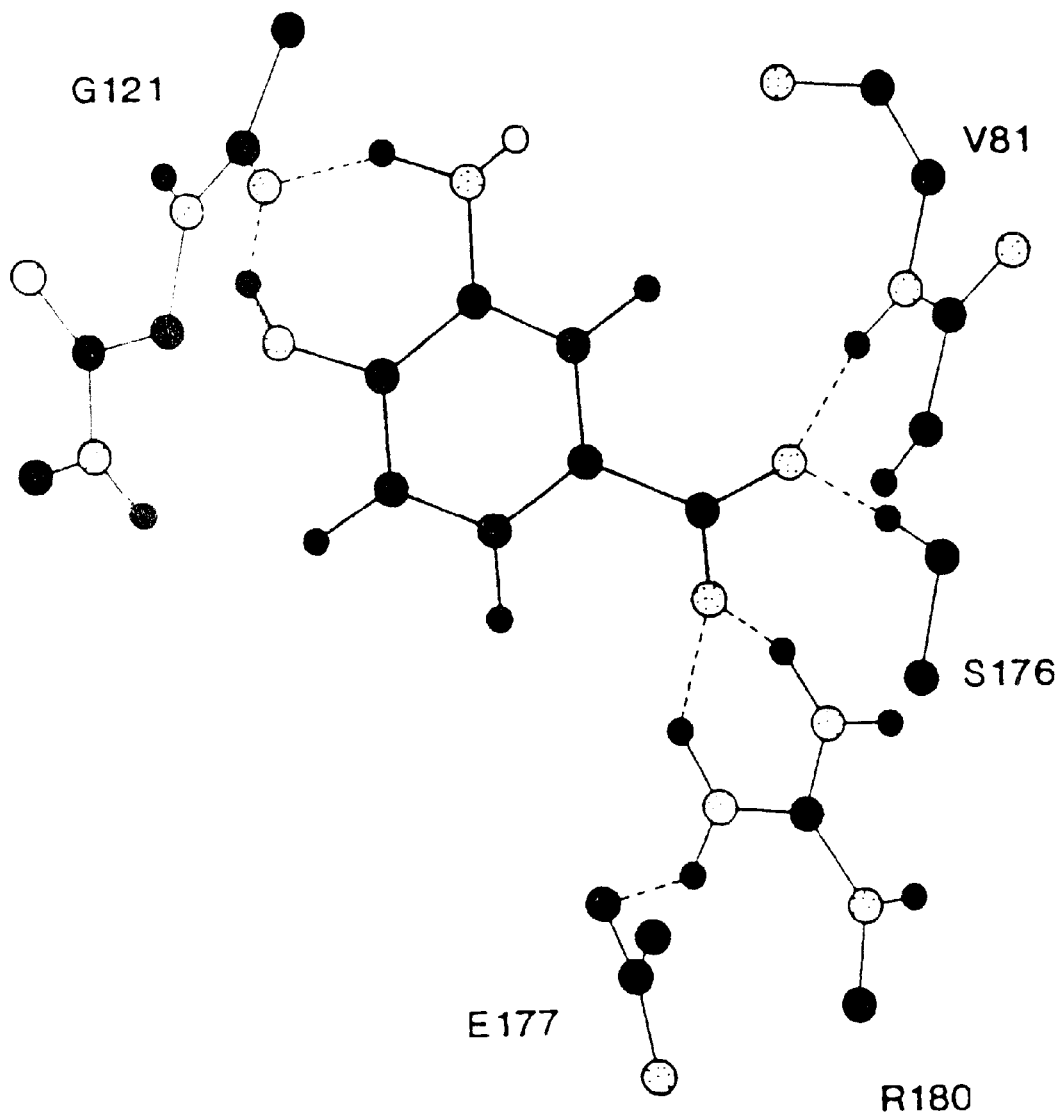

Table 3 shows the interaction energies of AHA and emodin with RTA to be relatively strong, based on molecular mechanics. Although they are predicted to bind well to RTA, they have quite different interaction geometry compared with adenine, pterin, and formycin. The putative binding of AHA is shown in FIG. 11f. Attempts to soak these highly colored compounds into RTA crystals failed, showing that a strong interaction energy is not sufficient to assure ligand binding.

In summary, the RTA specificity site is formed largely by the backbone of residues Gly 121, Asn 122, Tyr 123 and Val 81, and by side chains of Arg 180, Tyr 80, Tyr 123, Glu 177, and Trp 211. The interaction energy from hydrogen bonds is a major factor in determining RTA substrate specificity, and in particular at recognizing one adenine base in a particular rRNA context. The main donors and acceptors of RTA binding site to a base are the carbonyls of Gly 121 and Val 81, the amine of Val 81 and the side chain Arg 180. Obviously, the carbonyls and backbone amides are not flexible. The Arg 180 chain is not flexible either, because it forms an aromatic stack with Trp 211 and is strongly fixed by hydrogen bonds with the carboxylate of Glu 177 and the peptide carbonyl of Asn 78. The guanidinium side chain can move only within very limited space, and in the minimizations of the present invention, it always maintains its geometry. Taken together, this suggests that the RTA active site has evolved to act as a fairly rigid receptor to bind specific, complementary ring structures bearing a resemblance to adenine. It is possible to bind compounds, like pterins, which make additional contacts and have stronger interaction energies with the active site. This is an important consideration in inhibitor design. RTA has evolved to recognize an extended rRNA substrate and its strong binding to ribosomes (Km ~1 $\mu$M) arises partly from interactions at sites remote from the catalytic adenine recognition site. It is these areas that may need to be targeted for optimum inhibitor design.

EXAMPLE 6

Phage Display and Inhibitor Design

In addition to query-based search methods, phage display search methods are used to identify peptides which bind strongly to RTA and Shiga toxin. The method is useful in inhibitor/drug design in two ways. First, peptides can be identified that inhibit the toxins directly. Second, the crystal structure of tight-binding peptides likely reveals novel enzyme•ligand interactions since the peptides differ markedly from the heterocyclic systems observed crystallographically. The novel interactions identified are then fed into the query-based searches.

The principles of the phage display method are generally well known (Clackson and Wells, TIBTech 12:173–84 (1994)). M13 are filamentous phage with a major coat protein called P8 and a surface protein P3 involved in infectivity; both proteins have been engineered for phage display. P3 is localized at one end of the phage and is present in only 3 to 5 copies; the amino terminus of P3 can accommodate large peptide inserts without interfering with folding or infectivity. A commercial library was obtained from New England Biolabs containing all of the $1.3 \times 10^9$ (=$20^7$) random heptapeptides displayed on P3. This is about the upper limit of library size, given current transformation efficiencies for E. coli, and the limits of convenient handling of cell volumes. The manufacturer's simplest protocol for screening suggests attaching RTA to the wells of a microtiter plate via nonspecific hydrophobic interactions.

Roughly $10^{11}$ phage (about 100 copies of each displayed heptamer) were applied and allowed to bind. Those with poor binding were simply rinsed away. The tighter binding phage were then eluted, as suggested, using free RTA. The eluted phage were amplified in E. coli, titered, and used in a second screening round. A total of four rounds were carried out, presumably selecting for stronger binding peptides (the phage were eluted in rounds 3 and 4 using low pH instead of free RTA, as is discussed below). Ten phage from the last round were sequenced over the insert region, using the commercially available sequencing primer. Seven phage showed a consensus tetrapeptide sequence: Ser-(Ser/Thr)-(Leu/Ile)-Pro.

Native RTA is presented to the phage library, as opposed to RTA which has been nonspecifically adsorbed to microtiter plates. The standard RTA expression vector used in these experiments has been engineered to include coding for an amino terminal $His_6$ peptide. The His-tagged protein (his-RTA) is soluble and fully active and has been purified on standard Ni-NTA columns, indicating it binds Ni well. Microtiter plates obtained from QIAGEN Corporation coated with a Ni-NTA matrix binds the His-RTA to the wells through the His leader, displaying a fully active enzyme with its active site facing the solvent.

Phage binding to the RTA plates could be eluted with free RTA in rounds 1 and 2, but free RTA could not release phage in round 3. This has been interpreted to indicate that free RTA is not a strong enough competitor to release the peptide ligands and denaturation of RTA with low pH is required to allow phage elution. The implication is that the very strongest ligands were probably not released in the early rounds and were not amplified. Ultimately, peptides were selected with a clear affinity for RTA. Stronger stripping methods, such as low pH are used to identify better ligands.

Once a strongly-binding peptide is identified, it must be synthesized, being acetylated at the N terminus and amidated at the C terminus. The neutralization of the terminal charges minimize the chances of repulsion between the peptide and charged groups in the RTA active site. Once synthesized, the peptide is purified and tested as an inhibitor of RTA (for example, in the protein synthesis assay described in Example 1), and is then diffused into RTA crystals or cocrystallized with RTA for crystallographic examination as described in Example 2.

In addition to the linear-heptapeptide library, a cyclic peptide library may be utilized. A cyclic peptide is characterized by a fixed disulfide bond defining a loop of six random amino acids. The disulfide is flanked by at least one random amino acid on each end. Alternatively, a similar library is used, having four randomized residues in the loop, or having a random hexapeptide loop and four randomized residues flanking the disulfide. Cyclic peptides are advantageous in that they are structurally more rigid and constrained, and have greatly reduced flexibility compared to linear peptides. Binding of the corresponding free cyclic peptides to the enzyme target is entropically favorable compared with linear peptides and they tend to have stronger association constants. For example, it has been shown that the affinities of cyclic peptides for streptavidin exceed those of similar linear peptides by 100–1000 fold (Giebel,. et al., *Biochemistry* 34:15430–35 (1995). Further, X-ray structures confirm the notion that the cyclic peptides are more compact and constrained in the active site.

EXAMPLE 7

Inhibitor Design for STA1

Inhibitor design for STA1 follows the paths described in the Examples above for RTA; that is, computer searches, kinetic assays and phage display techniques are utilized. The plasmid pSC25 expresses STA. A stop codon is engineered into this plasmid at a position to produce the 32 kD active STA1 peptide, removing the inhibiting STA2 peptide instead of cleaving it with proteases. The engineered 28 kD protein is expressed and isolated for crystallization experiments. Further, a polyHis sequence is engineered to both the N and C termini of STA1, which expedites purification and allows for isolation of useful crystals since each modified construct represents an independent protein, as far as crystallization is concerned. Such tags attached to RTA did not hamper full enzymatic activity, and it is likely that identical tags will not hamper STA1 enzymatic activity. The work described above has provided a model of STA that is used for structure-based drug design; however, a workable crystal model of STA makes the best use of the iterative crystallographic algorithm of drug design.

Expression of the STA1 protein in the engineered pSC25 allows for kinetic tests to be carried out on various inhibitors. Obviously, due to the similarities between STA1 and RTA, it makes sense to try inhibitors on STA1 that have been identified as being effective on RTA. For example, pteroic acid inhibits RTA, and is tested on STA1. There are, however, differences between RTA and STA1 that potentially are important. Gly 121 is a key residue in the RTA active site, since its carbonyl group receives a hydrogen bond from the 2 amino group of pteroic acid. The corresponding residue in STA1 is Ser 112, and the disposition of the Ser side chain suggests that it may also interact with pteroic acid. However, the Ser 112 hydroxyl can form an additional bond, donating to N8 of the inhibitor, that is not formed by the RTA Gly, suggesting that pteroic acid may bind to STA1 more effectively that it does to RTA.

EXAMPLE 8

Synthetic Approach to Identifying Inhibitors

Once compounds are identified though the above-referenced computer modeling, crystallographic, energy minimization, phage display or protein synthesis assay means, the compounds are synthesized. A recent advance in synthetic organic chemistry involves the multiple simultaneous (multiplex) synthesis of an analogous series of compounds. Rather than performing one to three reactions in a given day, 30–100 reactions are run using an appropriate reaction manifold. The key is the purification of the individual products, which can be facilitated by supporting the fixed reagent on an insoluble polymer allowing simple filtration, followed by cleavage of the product from the support.

Alternatively, polymer-supported reagents are used to affect coupling of the two reactants, or to scavenge side-products, thereby converting them to insoluble material, which is easily separated from the reaction mixture by filtration. In yet another alternative, solution-phase chemistry is employed, followed by standard aqueous work-up procedures or selective crystallization of the of the product from the reaction mixture.

A relatively inexpensive apparatus facilitating parallel syntheses and allowing temperature control, variable speed mixing, and the maintenance of an inert atmosphere over each reactor has been devised. Work-up and purification of the multiple reactions run in this apparatus is simplified by the use of a solid-supported scavenger which reacts with excess reagent to form an insoluble product that is easily separated from the reactions mixture by filtration. Between 10 and 100 mg of each product is synthesized. In addition to providing ample sample for biological evaluation, this allows each product's identity and purity to be assayed using NMR techniques.

Scheme 1 below shows one class of parallel synthesis starting with pteroic acid and using carbonyldiimidazole or oxalyl chloride coupling agents or solid-phase synthesis with the pteroic acid group attached through the 2-amino substituent to a polymer support. Scheme 2 shows a second example of multiplex synthesis using 2-pivaloyl-6-formylpterin as the starting material. Condensation of this material with a variety of amines leads to imine intermediates that are reduced to afford the 2-pivaloyl-protected analogs. Purification of these protected analogs is simplified by use of a polymer-supported reducing agent, which is removed by filtration. The protected analogs are subjected to mild deprotection conditions and isolated by crystallization.

In parallel with the multiplex synthesis approach, traditional synthetic techniques are employed to prepare analogs of compounds identified as effective in inhibiting RTA or STA1. For example, analogs of pteroic acid in which the pterin moiety is replaced with an alternative heterocycle are prepared. Focus is on heterocycles predicted to adopt a tautomeric structure with strong binding to the adenine specificity pocket. The hydrogen binding properties of pterin (3) are present, but do not have to undergo an energetically unfavorable tautomerization. The structure below shows the generalized form of a series of these compounds. In this series, the steric and hydrogen bonding potential about the sulfur is varied systematically by manipulating the oxidation state from the sulfide to sulfoxide to sulfone.

Additional changes in the hydrogen bonding potential are explored by examining both the 1,2,4-benzothiadiazine (I, X —CH) and 1,2,4-pyridothisadiazine 1,1-dioxides; the preferred tautomeric form in solution is the 4-H form shown in structure I. An additional advantage to these compounds when compared to pteroic acid is increased aqueous solubility. In addition, modeling within the RTA specificity site suggests that the polar interaction between the sulfone group ($Y=SO_2$) and Arg 180 is substantially stronger than those made to the 4-oxo group of PTA. Finally, when developing inhibitors into drugs, it is important to note that compounds identified may bear a strong resemblance to known and approved compounds; for example, the compounds described above resemble benzothiadiazine diuretics like Aldactazine and Diuril.

The synthesis of compounds of general structure I proceeds based upon literature precedence. A general route to 2-amino-substituted 1,2,4-benzothiadiazines involving displacement of a 3-methylthio group has been reported by Pirotte, et al, *J.Med. Chem.* 36:3211–13 (1993); and Tullio et al, *Tetrahedron* 51:3221–34 (1995) have demonstrated the synthesis of 3-amino-substituted [2,3] pyrido-1,2,4-thiadiazines from 3-amino-2-sulfamoylpyridine, as shown in Scheme 3. Although 1,2,4-pyridothisdiazine-1,1-dioxides are known, there have not been reports of 1,2,4-pyridothisdiazines in which the sulfur is not oxidized, or is in the sulfoxide oxidation state. However, Finch et al., *J. Org. Chem.* 45:3416–21 (1980) reported routes to the corresponding 1,2,4-benzothiadiazines and 1,2,4,-benzotthisdiasine 1-oxides, Scheme 4. Adaptation of these rounds allows production of the corresponding pyrido-analogs.

EXAMPLE 9

Binding Interactions of Small Ring Compounds With the RTA Active Site

Computer-aided search methods, as described supra, indicated the compounds based on the pterin group act as inhibitors of ricin. For example, pteroic acid acts as a modest inhibitor with an $IC_{50}$ of about 0.6 mM (Yan, X., et al., *J. Mol. Biol*, 266:1043–1049 (1997)). A series of computations on the binding interactions of small ring compounds with the RTA active site helped in the creation of a chemical template of the active site to aid in further drug design (Yan, X., et al., *Proteins,* 31:33–41 (1998)). The results are shown in Table 4 below. The data clearly demonstrate that the pterin(3) tautomer binds better than formycin, which is in agreement with kinetic and crystallographic results; it is further suggested that guanine compounds, in the correct orientation, may be effective inhibitors.

TABLE 4

Interaction energy in kcal/mol between RTA and small ring compounds

| Compound | Aqueous phase energy | Solvation energy (SE) | RTA Interaction Energy | | | |
|---|---|---|---|---|---|---|
| | | | vdw (IE–SE) | Elec | Total (IE) | Net |
| formycin | 84.6 | −20.8 | −19.2 | −24.5 | −43.7 | −22.9 |
| adenine(1) | 63.7 | −23.1 | −18.0 | −19.4 | −37.4 | −14.3 |
| adenine(2) | 69.9 | −23.6 | −19.0 | −20.5 | −39.5 | −15.9 |
| Pterin(1) | 26.6 | −23.6 | −23.1 | −22.0 | −45.1 | −21.5 |
| pterin(2) | 33.4 | −21.8 | −22.8 | −21.8 | −44.6 | −22.8 |
| pterin(3) | 30.5 | −25.2 | −22.6 | −31.8 | −53.4 | −28.2 |
| pterin(4, ion) | −62.4 | −75.0 | −22.9 | −24.6 | −47.5 | −27.5 |
| guanine(1) | 22.1 | −26.8 | −18.7 | −16.1 | −34.8 | −8.0 |
| guanine(2) | 27.4 | −22.1 | −21.8 | −20.0 | −40.8 | −18.7 |
| guanine(3) | 30.0 | −25.3 | −20.8 | −33.0 | −53.8 | −28.5 | vdw - van der Waals interaction energy (kcal/mol)

EXAMPLE 10

Figure 15:
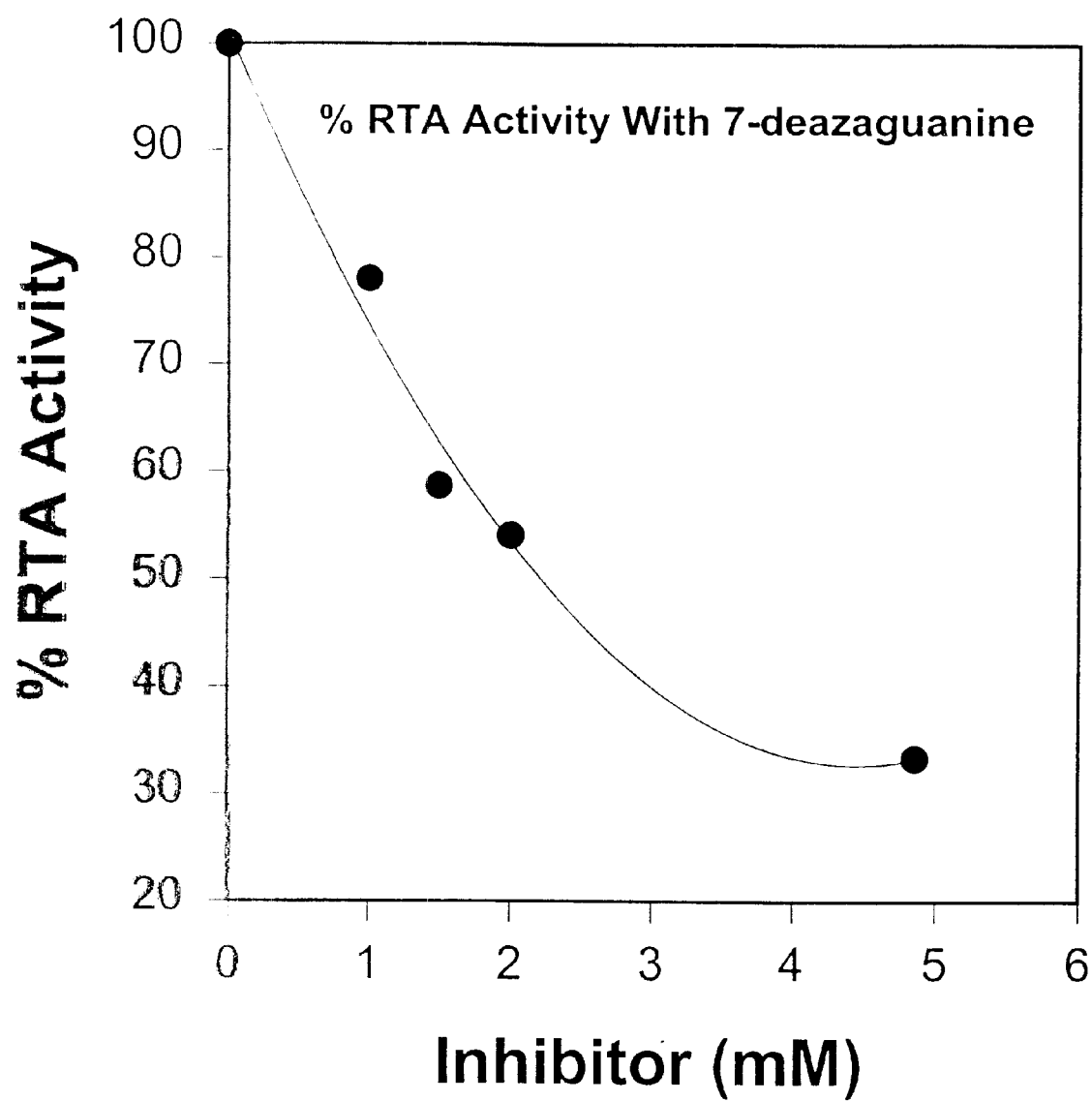
FIG. 15 depicts the RTA activity of 7-deazaguanine. RTA activity is plotted versus inhibitor concentration.

Potency of Guanine-based compounds as RTA Inhibitor,

To test the potency of guanine-based compounds, 7-deazaguanine was synthesized using published methods. This compound, shown in FIG. 15, is aimed at binding to the specificity pocket of RTA to occupy the area which binds adenine or RNA substrates.

EXAMPLE 11

Synthesis of a Novel PTA Analog

Figure 14:
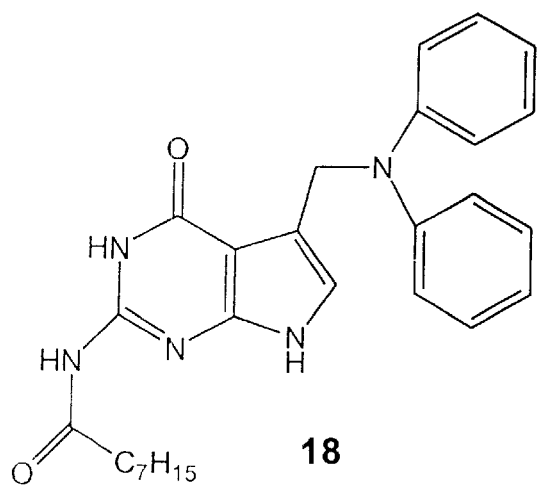
FIG. 14 illustrates the synthesis of the novel pteroic acid analog BMR09 (2-amino-5-[(4'-benzoyl)methylamino]-3,4-dihydro-4-oxo-7H-pyrrolo[2,3-d]pyrimidine).
Figure 14:
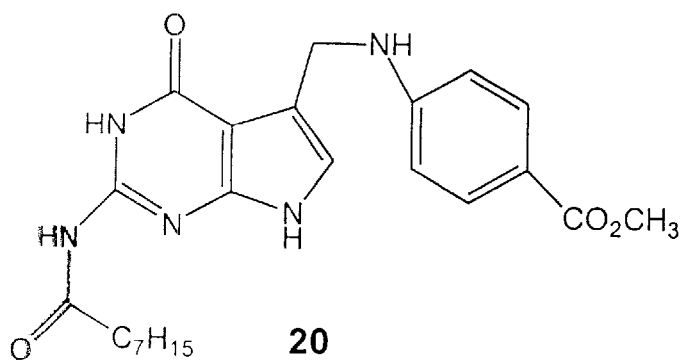
Figure 14:
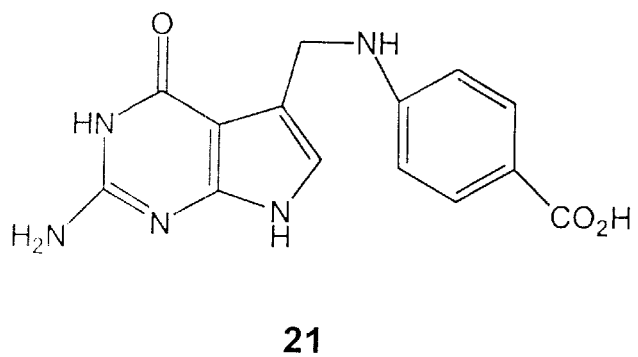

A novel compound #21, which is an analog of PTA, was synthesized. FIG. 14 is an illustration of the synthesis of this new compound, which contains the 7-deazaguanine moiety.

The steps in the synthesis of Compound #21 are as follows: A suspension of compound #18 (220 mg, 0.412 mmol) and methyl 4-aminobenzoate, compound #19 (331.2 mg, 2.06 mmol) in 1.5 ml of methanol:THF (1:1). The reaction was carried out in a sealed tube at 70° C. for 24 hours with stirring. The reaction mixture was cooled to room temperature and evaporated to dryness. The residue was applied to a silica gel chromatography column and washed with 200 ml of chloroform:methanol (95:5). The product was eluted with chloroform:methanol (90:10) to yield 98 mg (54%) of compound #20 as an off-white solid.

Compound #20 can be further characterized chemically as follows: TLC $R_f$ 0.39 (CHCl$_3$:MeOH, 90:10); $^1$H NMR (DMSO-d$_6$)_7.66 (d, 10 Hz, 2H, C$_6$H$_4$), 6.88 (s, 1H, 6-CH), 6.77 (t, 6Hz, 1H, 2-NH), 6.64 (d, 10 Hz, 2H, C$_6$H$_4$), 4.39 (bd, 2H, 5-CCH$_2$NH), 3.72 (s, 3H, CO$_2$CH$_3$), 2.42 (t, 2H, C$_7$H$_{15}$), 1.56 (bt, 2H, C$_7$H$_{15}$), 1.26 (bs, 8H, C$_7$H$_{15}$), 0.90 (bt, 3H, C$_7$H$_{15}$); MS (CI$^+$) 440.14 (M+H$^+$); HRMS (CI$^+$) 439.221475 (C$_{23}$H$_{29}$N$_5$O$_4$), Calculated Mass 439.221955.

The synthesis of compound #21, proceeded as follows: To a solution of compound #20 (103 mg, 0.234 mmol) in 500 μl of EtOH and 2 ml of H$_2$O was added 5 M KOH (117.25 μl, 0.586 mmol). This mixture was stirred for 48 hours, at which time the reaction became homogeneous. The solution was evaporated and the residue taken up in H$_2$O and the pH adjusted to 7. The H$_2$O was removed in vacuo and the residue was taken up in MeOH. The mixture was centrifuged and the MeOH was removed. More MeOH was added; this process was carried out three times. The MeOH fractions were combined, evaporated and the residue applied to a flash silica gel chromatography column and eluted with CHCl$_3$:MeOH:AcOH (90:9:1). 6.2 mg (95) of compound #21 was isolated as a yellow solid. Compound #21 can be further chemically characterized: TLC $R_f$ 0.09 (CHCl$_3$:MeOH:AcOH, 90:9:1); $^1$H NMR (D$_2$O)_7.64 (d, 10 Hz, 2H, C$_6$H$_4$), 6.79 (d, 10 Hz, 2H, C$_6$H$_4$), 6.61 (s, 1H, 6-CH).

EXAMPLE 12

Inhibition of RTA by 7-Deazqaguanine and Compound #21

Figure 16:
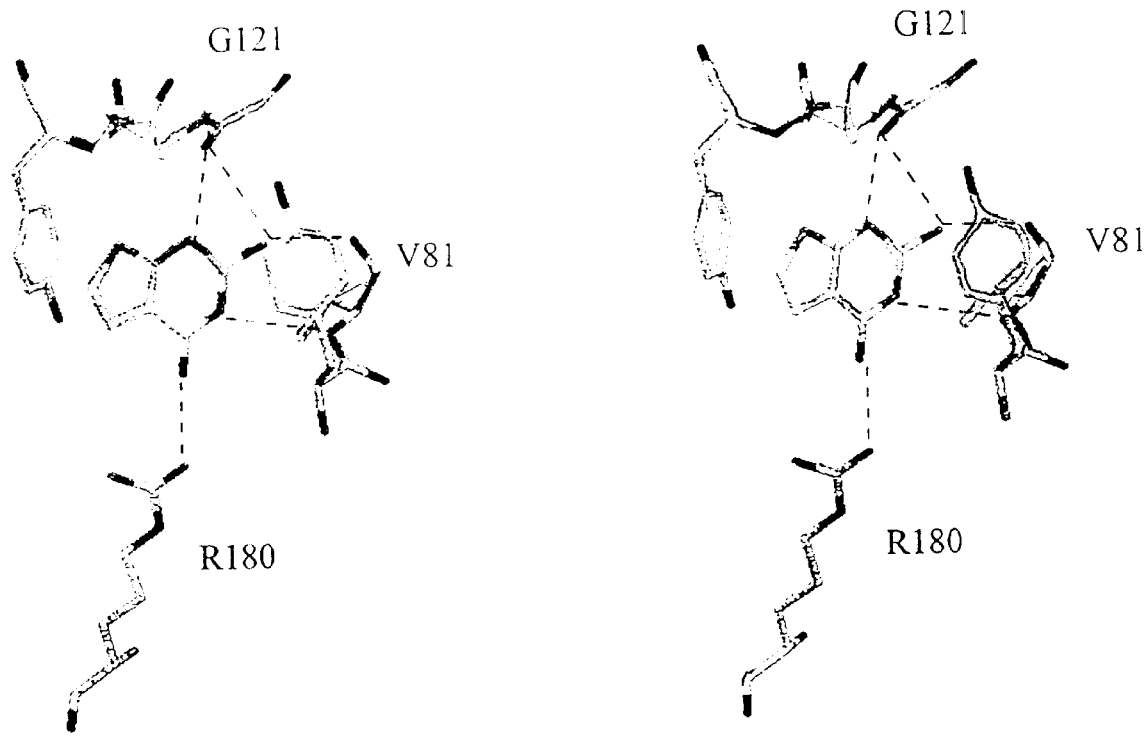
FIG. 16 shows a stereogram of the binding of 7-deazaguanine to the ricin A chain.

The potency of these compounds to inhibit RTA action against ribosomes was tested. The same methods as described supra were used (see Examples 4 and 5). 7-deazaguanine is thought to occupy only the specificity site; it is the first compound of its size to give measurable inhibition of RTA. The IC$_{50}$ was about 1.5 mM. It is the best specificity pocket binder seen thus far. A plot of RTA activity versus inhibitor concentration is shown in FIG. 15. FIG. 16 shows a stereogram representing the binding of 7-deazaguanine to RTA.

Compound #21 was also tested and it was found to be the best inhibitor of RTA identified to date. Preliminary tests suggest that the IC$_{50}$ for this inhibitor is about 0.3 mM. This implies that a 7-deazaguanine moiety is a better framework than the pterins on which to construct RTA and STA inhibitor compounds. It is also possible to make longer pendent versions of compound III which will go into the "second pocket". That is, in addition to nonpolar interactions, one can make specific polar interactions.

EXAMPLE 13

Synthesis of Additional Ricin Chain Inhibitors

Figure 17:
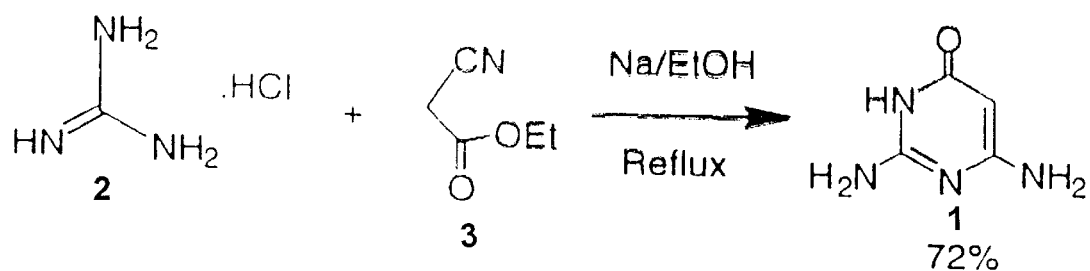
FIG. 17 shows the synthesis scheme for 2,6-diamino-3H-pyrimidin-4-one 1.

FIG. 17 shows the synthesis of 2,6-diamino-3H-pyrimidin-4-one 1. 2,6-diamino-3H-pyrimidin-4-one 1 was synthesized from guanidine 2 and ethylcyano acetate 3 by reflux in the presence sodium and ethanol.

Preparation of α-tosyloxy Acetone

Zheng, L.; Berridge, M. S.; Ernsberger, P. *J. Med. Chem.*, 1994, 37, 3219

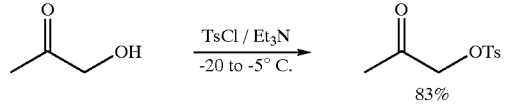

α-Hydroxy acetone (7.41 g, 0.1 mol) was dissolved in dry Et$_3$N (100 mL) and cooled to −20° C. TsCl (21.9 g, 0.12 mol) in dry CH$_2$Cl$_2$ (50 mL) was added slowly in such a way that the temperature was maintained below −5° C. After complete addition of TsCl, the reaction mixture was washed with water (200 mL), aq. 6N HCl (100 mL), water (200 mL) and dried over MgSO$_4$. Filtration followed by evaporation of solvent afforded the crude product which was chromatographed on silica gel (20% EtOAc/Hexane) afforded the product as a colourless oil. Yield: 17.7 g, 83% $^1$H NMR (300 MHz, DMSO-d$^6$): δ 2.20 (s, 3H), 2.46 (s, 3H), 4.49 (s, 2H), 7.36–7.82 (AA'BB' J=7.8 Hz, 4H) $^{13}$C NMR (75 MHz, DMSO-d$^6$): δ 21.6, 26.4, 71.9, 127.9, 130.0, 132.2, 145.5, 201.0 HRMS (CI) Calculated for CHXNO 2-Amino-6-Methyl-3,4-dihydro-4-oxo-7H-pyrrolo[2,3-d] Pyrimidine:

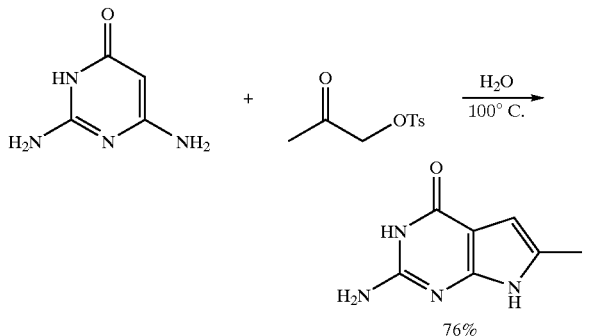

76%

A mixture of 2,6-diamino-4-hydroxypyrimidine (6.30 g, 50 mmol) and NaOAc (4.1 g, 50 mmol) in water (150 mL) was heated to 100° C. to form the homogeneous solution. α-tosyl acetone (4.70 g, 50 mmol) was added all at once and stirred further at 100° C. for 5 hours. The reaction mixture was cooled to 4° C. and filtered to afford the product as a pink coloured solid. The solid was heated to 100° C. under vacuum to afford buff colored solid. Yield: 5.42 g, 66%, R$_f$: 0.37 (20% MeOH/CHCl$_3$) $^1$H NMR (300 MHz, DMSO-d$^6$): δ 2.13 (d, J=0.9 Hz, 3H), 5.82 (q, J=0.9 Hz, 1H), 5.93 (br s, 1H), 10.10 (br s, 1H), 10.77 (br s, 1H). HRMS (CI) Calcd for C$_7$H$_9$N$_4$O 165.0776; Found: 165.0773. The spectral data are compatible with an authentic sample.

Mechanism:

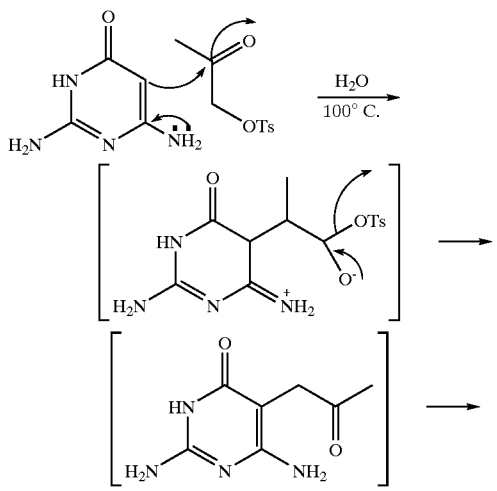

-continued

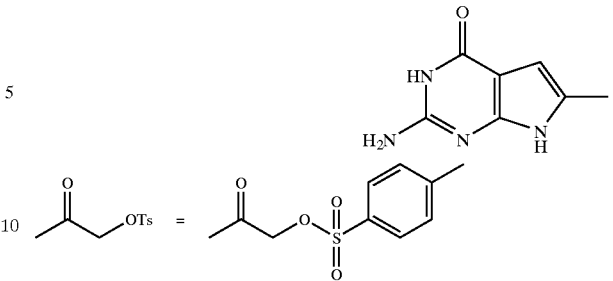

Figure 18:
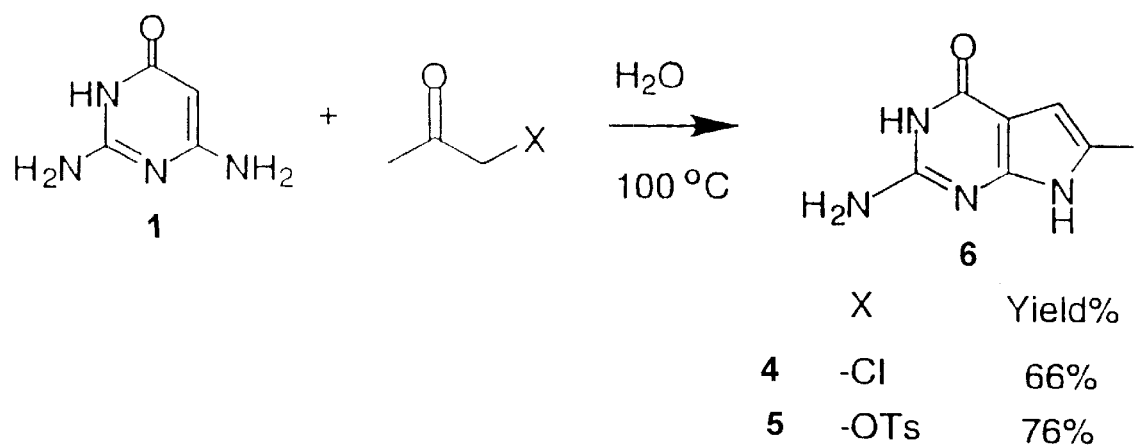
FIG. 18 shows the α-chloroketone based synthesis of octanoic acid(7-octanoyl-4-oxo-4,7-dihydro-3H-pyrrolo[2,3-d]pyrimidin-2-yl)-amide 16 from 2,6-diamino-3H-pyrimidin-4-one 1.

The synthesis method is summarized in FIG. 18. α-chloroacetone 4 and α-tosyloxyacetone 5 were used as the ketone derivatives. Use of α-tosyloxyacetone 5 resulted in a yield of 76% as opposed to a 66% when α-chloroacetone 4 was used as the ketone derivative.

Figure 19:
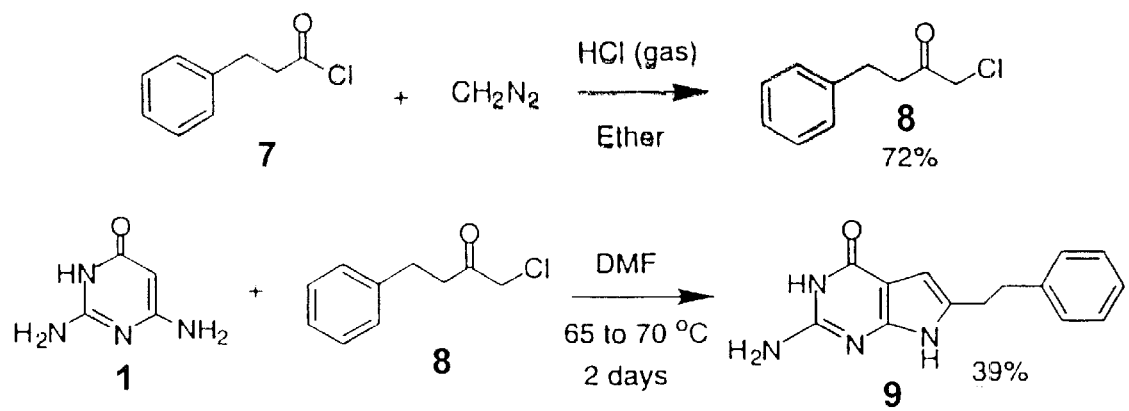
FIG. 19 shows the α-chloroketone based synthesis of 2-amino-6-phenethyl-3,7-dihydro-pyrrolo[2,3-d]pyrimidin-4-one 9.

FIG. 19 presents the method used to synthesize 2-amino-6-phenethyl-3,7-dihydro-pyrrolo[2,3-d]pyrimidin-4-one 9. Phenylpropanoyl chloride7 was reacted with CH$_2$N$_2$ in the presence of gaseous hydrogen chloride and ether to produce 1-chloro-4-phenyl-2-butanone 8. 1-chloro-4-phenyl-2-butanone 8 was reacted with 2,6-diamino-3H-pyrimidin-4-one 1 to produce 2-amino-6-phenethyl-3,7-dihydro-pyrrolo[2,3-d]pyrimidin-4-one 9 at a 39% yield.

Figure 20:
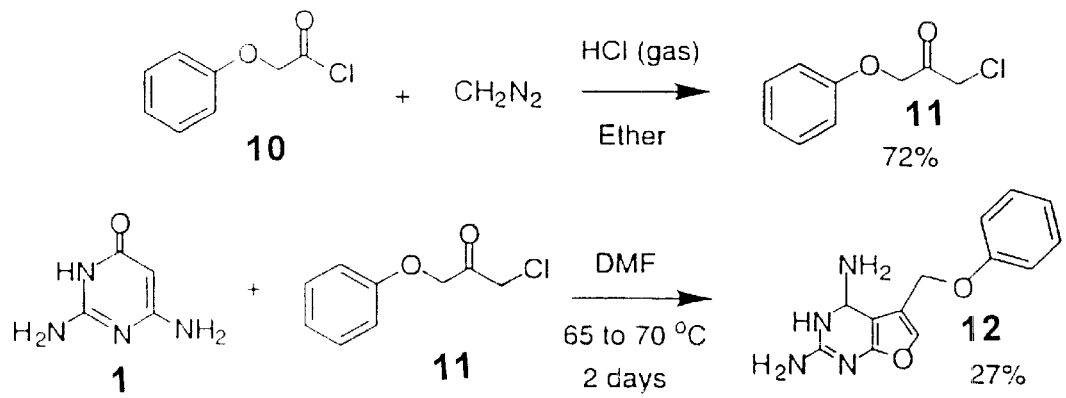
FIG. 20 shows the method of synthesis for 2,6-diamino-5-bromopyrimidin-4-one 13.

The synthesis of 2,4-diamino-4-phenoxymethylfuro[2,3-d]pyrimidin-4-one12 is shown in FIG. 20. Phenoxyacetyl chloride 10 was reacted with CH$_2$N$_2$ in the presence of gaseous hydrogen chloride and ether to produce 1-chloro-3-phenoxy-2-propanone 11. 1-chloro-3-phenoxy-2-propanone 11 was reacted with 2,6-diamino-3H-pyrimidin-4-one 1 to produce 2,4-diamino-4-phenoxymethylfuro[2,3-d]pyrimidin-4-one 12 at a 39% yield.

Figure 21:
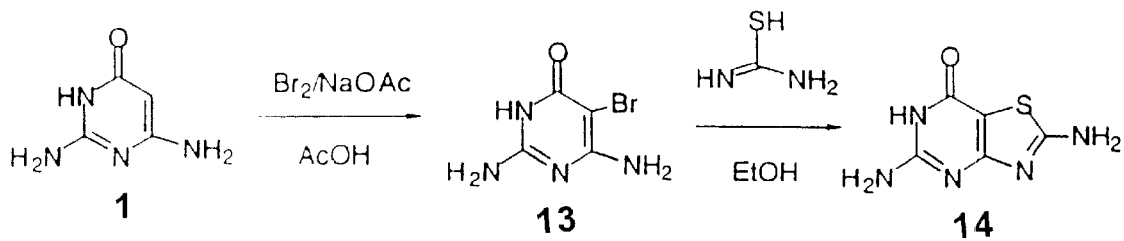
FIG. 21 shows the method of synthesis for 2,5-diamino-6H-thiazolo[4,5-d]pyrimidin-7-one 14 from 2,6-diamino-3H-pyrimidin-4-one 1.

FIG. 21 shows the method of synthesis of 2,5-diamino-6H-thiazolo[4,5-d]pyrimidin-7-one 14. 2,6-diamino-3H-pyrimidin-4-one 1 was reacted with Br$_2$ in the presence of sodium acetate and acetic acid to produce 2,6-diamino-5-bromopyrimidin-4-one 13. 2,6-diamino-5-bromopyrimidin-4-one 13 was then reacted with CN$_2$SH$_4$ in ethanol to produce 2,5-diamino-6H-thiazolo[4,5-d]pyrimidin-7-one 14.

Figure 22A:
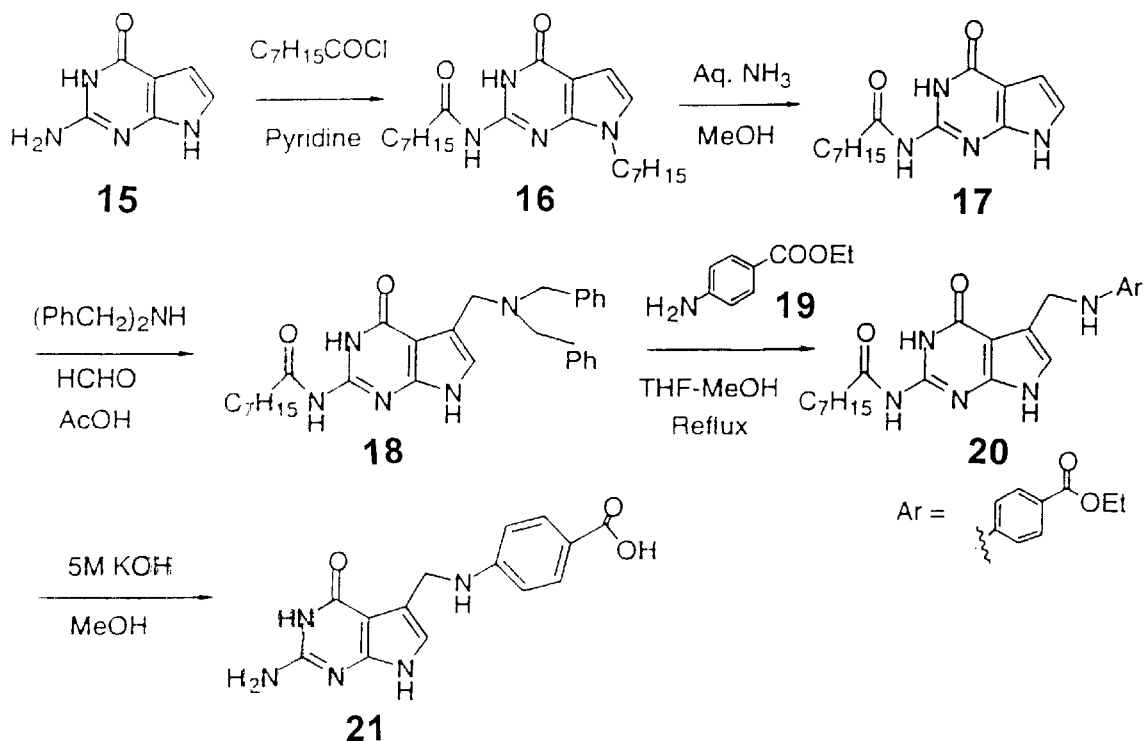
FIGS. 22A and 22B show the methods of synthesis for 4-[(2-amino-4-oxo-4,7-dihydro-3H-pyrrolo[2,3-d]pyrimidin-5-ylmethyl)-amino]-benzoic acid 21 and 2-amino-5-{[4-(4-amino-benzyl)-phenylamino]-methyl}-3,7-dihydro-pyrrolo[2,3-d]pyrimidin-4-one 24 from guanine.
Figure 22B:
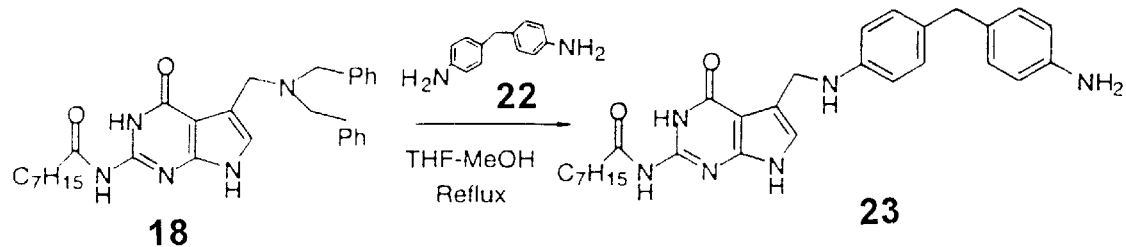
Figure 23:
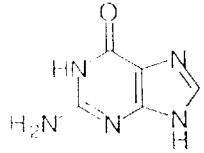
FIG. 23 shows the results of the inhibition of ricin chain A with various inhibitors.
Figure 23:
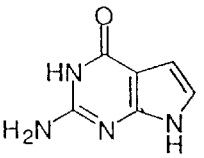
Figure 23:
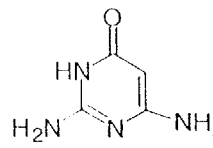
Figure 23:
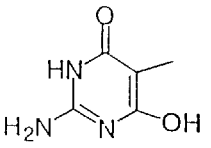
Figure 23:
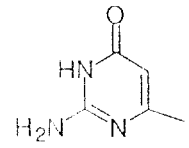
Figure 23:
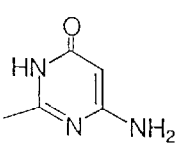
Figure 23:
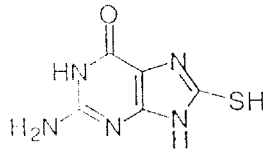
Figure 23:
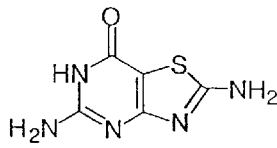
Figure 23:
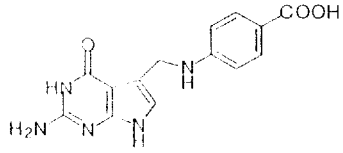
Figure 23:
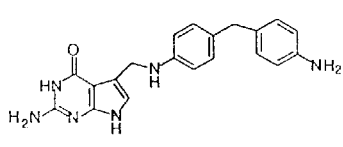
Figure 23:
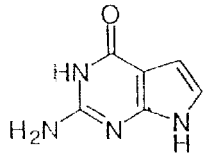
Figure 23:
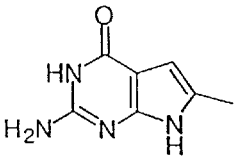

The syntheses of 4-[(2-amino-4-oxo-4,7-dihydro-3H-pyrrolo[2,3-d]pyrimidin-5-ylmethyl)-amino]-benzoic acid 21 and 2-amino-5-{[4-(4-amino-benzyl)-phenylamino]-methyl}-3,7-dihydro-pyrrolo[2,3-d]pyrimidin-4-one 24 are shown in FIG. 22. FIG. 22A details the synthesis of 4-[(2-amino-4-oxo-4,7-dihydro-3H-pyrrolo[2,3-d]pyrimidin-5-ylmethyl)-amino]-benzoic acid 21. 2-amino-3,7-dihydro-pyrrolo[2,3-d]pyrimidin-4-one 15 is reacted with octanoyl chloride in pyridine to produce octanoic acid(7-octanoyl-4-oxo-4,7-dihydro-3H-pyrrolo[2,3-d]pyrimidin-2-yl)-amide 16, which is then treated with ammonia in methanol to produce octanoic acid(4-oxo-4,7-dihydro-3H-pyrrolo[2,3-d]pyrimidin-2-yl)-amide 17. Octanoic acid(4-oxo-4,7-dihydro-3H-pyrrolo[2,3-d]pyrimidin-2-yl)-amide 17 is reacted with (PhCH$_2$)$_2$NH in formaldehyde to produce octanoic acid{5-[(dibenzylamino)-methyl]-4-oxo-4,7-dihydro-3H-pyrrolo[2,3-d]pyrimidin-2-yl}-amide 18. Octanoic acid{5-[(dibenzylamino)-methyl]-4-oxo-4,7-dihydro-3H-pyrrolo[2,3-d]pyrimidin-2-yl}-amide 18 is reacted with 4-amino-methylbenzoate 19 to yield 4-[(2-octanoylamino-4-oxo-4,7-dihydro-3H-pyrrolo[2,3-d]pyrimidin-5-ylmethyl)-amino]-benzoic acid methyl ester 20. Treatment of 4-[(2-octanoylamino-4-oxo-4,7-dihydro-3H-pyrrolo[2,3-d]pyrimidin-5-ylmethyl)-amino]-benzoic acid methyl ester 20 with 5 M KOH in ethanol yields 4-[(2- amino-4-oxo-4,7-dihydro-3H-pyrrolo[2,3-d]pyrimidin-5-ylmethyl)-amino]-benzoic acid 21.

The synthesis of 2-amino-5-{[4-(4-amino-benzyl)-phenylamino]-methyl}-3,7-dihydro-pyrrolo[2,3-d]pyrimidin-4-one 24 follows the same steps as the synthesis of 4-[(2-amino-4-oxo-4,7-dihydro-3H-pyrrolo[2,3-d]pyrimidin-5-ylmethyl)-amino]-benzoic acid 21, except that octanoic acid{5-[(dibenzylamino)-methyl]-4-oxo-4,7-dihydro-3H-pyrrolo[2,3-d]pyrimidin-2-yl}-amide 18 is reacted with 4,4'-methylene dianiline 22 to form octanoic acid (5-{[4-(4-amino-benzyl)-phenylamino]-methyl}-4-oxo-4,7-dihydro-3H-pyrrolo[2,3-d]pyrimidin-2-yl)-amide 23. Octanoic acid (5-{[4-(4-amino-benzyl)-phenylamino]-methyl}-4-oxo-4,7-dihydro-3H-pyrrolo[2,3-d]pyrimidin-2-yl)-amide 23 is then reacted with 5M KOH to form 2-amino-5-{[4-(4-amino-benzyl)-phenylamino]-methyl}-3,7-dihydro-pyrrolo[2,3-d]pyrimidin-4-one 24.

EXAMPLE 14

Inhibitor Design For RTA1: The Design of Additional Ricin A Chain (RTA) Inhibitors Based on the Pteroic Acid/RTA Complex The structural information obtained from the pteroic acid/ricin A chain complex was used to design additional molecules that exploit the pterin binding pocket consisting in part of residues G121, V81, R180 to design additional RTA inhibitors. PTA bound RTA X-ray structure revealed that the a more favorable interaction between RTA and the inhibitor could be made if the 6-membered pyrazine ring of the PTA were replaced with a 5-membered ring. Most of these molecules were derivative of guanine or structurally similar molecules. The results suggest that 2,6-diamino-3H-pyrimidin-4-one 1, 2-amino-6-dihydroxy-5-methylpyrimidin-4-one 25, 2-amino-6-methylpyrimidin-4-one 26, 6-amino-2-methyl-3H-pyrimidin-4-one 27, 2-amino-8-mercapto-1,9-dihydro-purin-6-one 28, 2,5-diamino-6H-thiazolo[4,5-d]pyrimidin-7-one 14, 4-[(2-amino-4-oxo-4,7-dihydro-3H-pyrrolo[2,3-d]pyrimidin-5-ylmethyl)-amino]-benzoic acid 21, 2-amino-5-{[4-(4-amino-benzyl)-phenylamino]-methyl}-3,7-dihydro-pyrrolo[2,3-d]pyrimidin-4-one 24, and 2-amino-6-methyl-3,7-dihydro-pyrrolo[2,3-d]pyrimidin-4-one 6 would be effective ricin A chain inhibitors.

The *Artemia salinas* ribosome in vitro protein synthesis assay was used to analyze the effects of 2,6-diamino-3H-pyrimidin-4-one 1, 2-amino-6-dihydroxy-5-methylpyrimidin-4-one 25, 2-amino-6-methylpyrimidin-4-one 26, 6-amino-2-methyl-3H-pyrimidin-4-one 27, 2-amino-8-mercapto-1,9-dihydro-purin-6-one 28, 2,5-diamino-6H-thiazolo[4,5-d]pyrimidin-7-one 14, 4-[(2-amino-4-oxo-4,7-dihydro-3H-pyrrolo[2,3-d]pyrimidin-5-ylmethyl)-amino]-benzoic acid 21, 2-amino-5-{[4-(4-amino-benzyl)-phenylamino]-methyl}-3,7-dihydro-pyrrolo[2,3-d]pyrimidin-4-one 24, and 2-amino-6-methyl-3,7-dihydro-pyrrolo[2,3-d]pyrimidin-4-one 6 on ricin activity. The results are presented in FIG. 23. 2-amino-6-methyl-3,7-dihydro-pyrrolo[2,3-d]pyrimidin-4-one 6 was the most effective inhibitor with an IC50 of 0.25 mM.

Table 5 shows a correlation of compound number, structure and compound name.

TABLE 5

| Compound | Structure | Name |
|---|---|---|
| 1. | 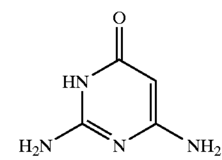  | 2,6-Diamino-3H-pyrimidin-4-one |
| 2. | 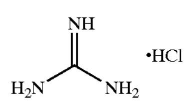  | Guanidine |
| 3. | 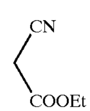  | Ethylcyano acetate |
| 4. | 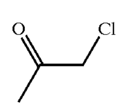  | α-chloroacetone |
| 5. | 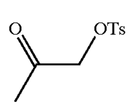  | α-tosyloxyacetone |
| 6. | 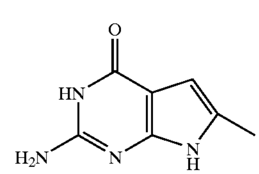  | 2-Amino-6-methyl-3,7-dihydro-pyrrolo[2,3-d]pyrimidin-4-one |

TABLE 5-continued

| Compound | Structure | Name |
|---|---|---|
| 7. | 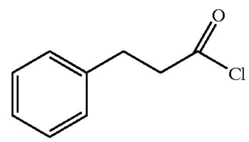 | Phenylpropanoyl chloride |
| 8. | 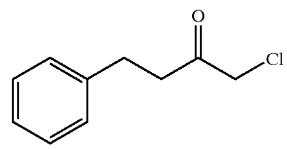 | 1-chloro-4-phenyl-2-butanone |
| 9. | 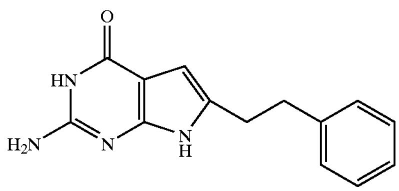 | 2-Amino-6-phenethyl-3,7-dihydro-pyrrolo[2,3-d]pyrimidin-4-one |
| 10. | 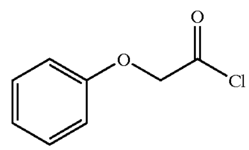 | Phenoxyacetyl chloride |
| 11. | 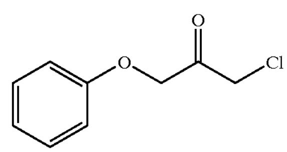 | 1-chloro-3-phenoxy-2-propanone |
| 12. | 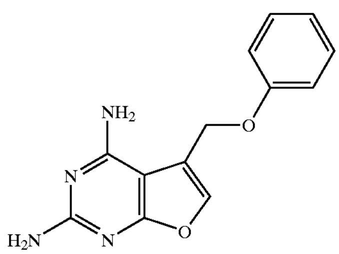 | 2,4-Diamino-4-phenoxymethylfuro[2,3-d]pyrimidin4-one |
| 13. | 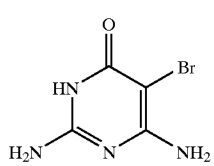 | 2,6-diamino-5-bromopyrimidin-4-one |
| 14. | 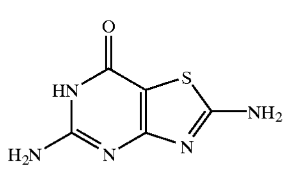 | 2,5-Diamino-6H-thiazolo[4,5-d]pyrimidin-7-one |

TABLE 5-continued

| Compound | Structure | Name |
| --- | --- | --- |
| 15. | 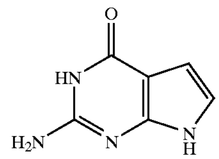 | 2-Amino-3,7-dihydro-pyrrolo[2,3-d]pyrimidin-4-one |
| 16. | 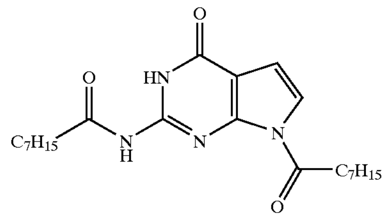 | Octanoic acid (7-octanoyl-4-oxo-4,7-dihydro-3H-pyrrolo[2,3-d]pyrimidin-2-yl)-amide |
| 17. | 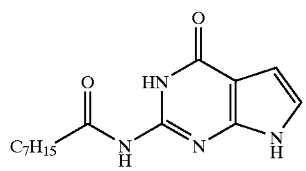 | Octanoic acid (4-oxo-4,7-dihydro-3H-pyrrolo[2,3-d]pyrimidin-2-yl)-amide |
| 18. | 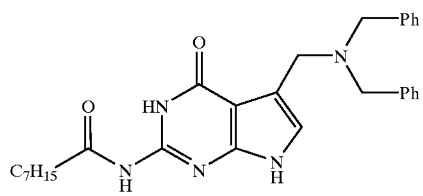 | Octanoic acid {5-[(dibenzylamino)-methyl]-4-oxo-4,7-dihydro-3H-pyrrolo[2,3-d]pyrimidin-2-yl}-amide |
| 19. | 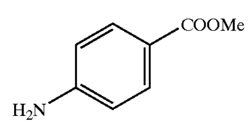 | 4-amino-methylbenzoate |
| 20. | 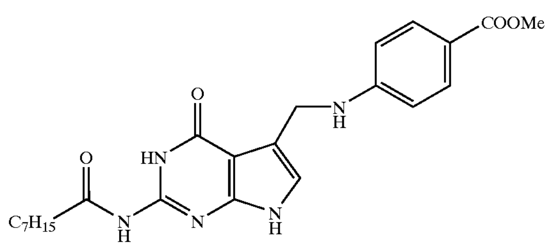 | 4-[(2-Octanoylamino-4-oxo-4,7-dihydro-3H-pyrrolo[2,3-d]pyrimidin-5-ylmethyl)-amino]-benzoic acid methyl ester |
| 21. | 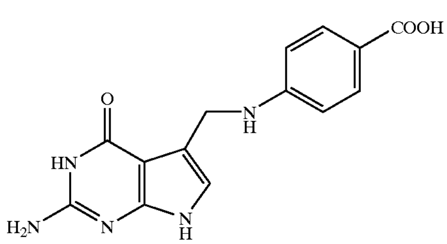 | 4-[(2-Amino-4-oxo-4,7-dihydro-3H-pyrrolo[2,3-d]pyrimidin-5-ylmethyl)-amino]-benzoic acid |
| 22. | 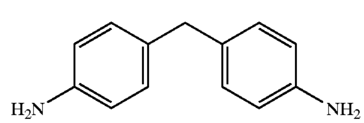 | 4,4'-methylene dianiline |

TABLE 5-continued

| Compound | Structure | Name |
|---|---|---|
| 23. | 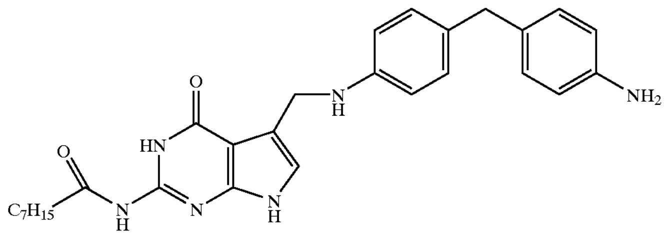 | Octanoic acid (5-{[4-(4-amino-benzyl)-phenylamino]-methyl}-4-oxo-4,7-dihydro-3H-pyrrolo[2,3-d]pyrimidin-2-yl)-amide |
| 24. | 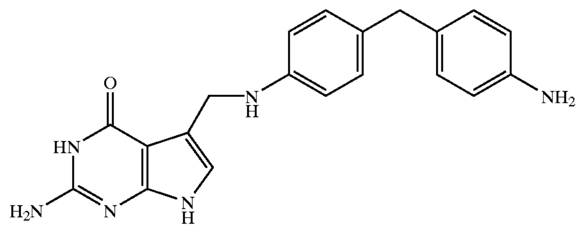 | 2-Amino-5-{[4-(4-amino-benzyl)-phenylamino]-methyl}-3,7-dihydro-pyrrolo[2,3-d]pyrimidin-4-one |
| 25. | 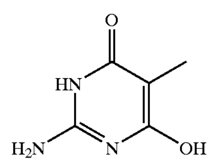 | 2-amino-6-dihydroxy-5-methylpyrimidin-4-one |
| 26. | 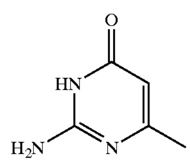 | 2-amino-6-methylpyrimidin-4-one |
| 27. | 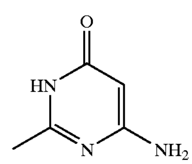 | 6-Amino-2-methyl-3H-pyrimidin-4-one |
| 28. | 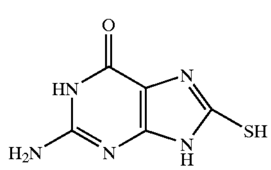 | 2-Amino-8-mercapto-1,9-dihydro-purin-6-one |
| 29. | 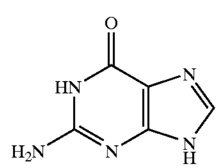 | Guanine |

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A compound having an aromatic heterocyclic molecular core that resembles an adenine moiety in size and shape, said compound inhibiting ricin or Shiga toxin;

wherein said compound is 2-amino-6-methyl-3,7-dihydro-pyrrolo[2,3-d]pyrimindin-4-one, 4-[(2-amino-4-oxo-4,7-dihydro-3H-pyrrolo[2,3-d]pyrimidin-5ylmethyl)-amino]benzoic acid or 2-amino-5-{[4-(4-amino-benzyl)-phenylamino]-methyl}-3,7-dihydro-pyrrolo[2,3-d]pyrimidin-4-one.

* * * * *

UNITED STATES PATENT AND TRADEMARK OFFICE
CERTIFICATE OF CORRECTION

PATENT NO. : 6,562,969 B1
DATED : May 13, 2003
INVENTOR(S) : Jon Robertus, Sean Kerwin and Xinjian Yan It is certified that error appears in the above-identified patent and that said Letters Patent is hereby corrected as shown below:

Column 1,
Line 56, please delete the comma after "bullet".

Column 2,
Line 44, "pressed" should read -- expressed --.

Column 4,
Line 33 and 37, "compounds" should read -- compound --.

Column 5,
Line 58, "Figure" should read -- figure --.

Column 7,
Line 10, please delete the second "refers to".
Line 42, please delete the ")" symbol.

Column 8,
Line 1, please delete the comma after "Fourier".

Column 11,
Line 11, please delete the perios after "detector".

Column 12,
Line 66, "ribosomes" should not be italicized.

Column 15,
Line 37, please insert a space between "80" and "side".
Line 39, "models" should read -- model --.
Line 60, please replace "accept" with -- except --.

Column 17,
Line 57, "Tautomehization" should read -- Tautomerization --.

Column 18,
Line 61, please delete the space in "b e".

Column 21,
Line 57, please delete the second instance of "of the".

UNITED STATES PATENT AND TRADEMARK OFFICE
CERTIFICATE OF CORRECTION

PATENT NO.     : 6,562,969 B1
DATED          : May 13, 2003
INVENTOR(S)    : Jon Robertus, Sean Kerwin and Xinjian Yan It is certified that error appears in the above-identified patent and that said Letters Patent is hereby corrected as shown below:

Column 22,
Line 66, "supra" should be italicized

Column 27,
Line 29, please delete the word "the".

Signed and Sealed this

Ninth Day of March, 2004

JON W. DUDAS
*Acting Director of the United States Patent and Trademark Office*